(12) United States Patent
Muratoglu et al.

(10) Patent No.: US 9,005,299 B2
(45) Date of Patent: Apr. 14, 2015

(54) METHODS AND DEVICES FOR KNEE JOINT REPLACEMENT WITH ANTERIOR CRUCIATE LIGAMENT SUBSTITUTION

(75) Inventors: Orhun K. Muratoglu, Cambridge, MA (US); Kartik Mangudi Varadarajan, Belmont, MA (US); Guoan Li, Milton, MA (US); Harry E. Rubash, Weston, MA (US); Thomas Zumbrunn, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 5 days.

(21) Appl. No.: 13/547,383

(22) Filed: Jul. 12, 2012

(65) Prior Publication Data

US 2013/0018477 A1    Jan. 17, 2013

Related U.S. Application Data

(60) Provisional application No. 61/507,434, filed on Jul. 13, 2011.

(51) Int. Cl.
| | |
|---|---|
| *A61F 2/38* | (2006.01) |
| *A61F 2/08* | (2006.01) |
| *A61F 2/30* | (2006.01) |

(52) U.S. Cl.
CPC ............... *A61F 2/3886* (2013.01); *A61F 2/08* (2013.01); *A61F 2/0811* (2013.01); *A61F 2/3836* (2013.01); *A61F 2002/30688* (2013.01)

(58) Field of Classification Search
CPC .................................................... A61F 2/3886
USPC ........................................... 623/20.14–20.36
See application file for complete search history.

(56) References Cited

U.S. PATENT DOCUMENTS

| | | | | |
|---|---|---|---|---|
| 4,034,418 A | * | 7/1977 | Jackson et al. | 623/20.3 |
| 4,224,696 A | * | 9/1980 | Murray et al. | 623/20.29 |
| 4,728,332 A | * | 3/1988 | Albrektsson | 623/20.29 |
| 4,911,721 A | * | 3/1990 | Albrektsson | 623/20.3 |
| 4,936,853 A | * | 6/1990 | Fabian et al. | 623/20.15 |
| 4,959,071 A | * | 9/1990 | Brown et al. | 623/20.27 |
| 5,047,057 A | * | 9/1991 | Lawes | 623/20.29 |

(Continued)

FOREIGN PATENT DOCUMENTS

| | | |
|---|---|---|
| EP | 2 248 488 A1 | 11/2010 |
| WO | 2011/071979 A2 | 6/2011 |

OTHER PUBLICATIONS

International Search Report and Written Opinion for Application No. PCT/US2012/046430, issued Jan. 23, 2013. (11 pages).

(Continued)

*Primary Examiner* — Alvin Stewart
(74) *Attorney, Agent, or Firm* — Quarles & Brady, LLP

(57) ABSTRACT

Methods and devices are provided for knee joint replacement with anterior cruciate ligament (ACL) substitution. Generally, the methods and devices can allow a knee joint to be partially or totally replaced in conjunction with substitution of the knee joint's ACL. In one embodiment, a knee replacement prosthesis can include a medial or lateral femoral implant, a femoral intercondylar notch structure, a medial or lateral tibial insert, and an ACL-substitution member. The ACL-substitution member can be configured to engage with the femoral intercondylar notch structure during a full range of knee motion and/or during only early knee flexion.

6 Claims, 37 Drawing Sheets

(56) References Cited

U.S. PATENT DOCUMENTS

| | | | |
|---|---|---|---|
| 5,147,405 A * | 9/1992 | Van Zile et al. | 623/20.27 |
| 5,192,328 A * | 3/1993 | Winters | 623/20.31 |
| 5,203,807 A * | 4/1993 | Evans et al. | 623/20.31 |
| 5,219,362 A * | 6/1993 | Tuke et al. | 623/20.31 |
| 5,282,870 A * | 2/1994 | Moser et al. | 623/20.31 |
| 5,370,699 A * | 12/1994 | Hood et al. | 623/20.28 |
| 5,879,400 A | 3/1999 | Merrill et al. | |
| 6,139,581 A * | 10/2000 | Engh et al. | 623/20.34 |
| 6,190,415 B1 * | 2/2001 | Cooke et al. | 623/20.33 |
| 6,235,060 B1 * | 5/2001 | Kubein-Meesenburg et al. | 623/20.31 |
| 6,406,497 B2 * | 6/2002 | Takei | 623/20.31 |
| 6,503,280 B2 * | 1/2003 | Repicci | 623/20.14 |
| 6,510,334 B1 * | 1/2003 | Schuster et al. | 600/407 |
| 7,060,101 B2 * | 6/2006 | O'Connor et al. | 623/20.32 |
| 7,166,650 B2 | 1/2007 | Muratoglu et al. | |
| 7,320,709 B2 * | 1/2008 | Felt et al. | 623/20.16 |
| 7,326,252 B2 * | 2/2008 | Otto et al. | 623/20.15 |
| 7,341,602 B2 * | 3/2008 | Fell et al. | 623/20.14 |
| 7,465,320 B1 * | 12/2008 | Kito et al. | 623/20.27 |
| 7,582,118 B2 * | 9/2009 | Brown et al. | 623/20.36 |
| 7,615,054 B1 * | 11/2009 | Bonutti | 606/88 |
| 7,678,152 B2 * | 3/2010 | Suguro et al. | 623/20.27 |
| 7,708,782 B2 * | 5/2010 | Burstein et al. | 623/20.33 |
| 7,815,684 B2 * | 10/2010 | McMinn | 623/20.27 |
| 7,875,081 B2 * | 1/2011 | Lipman et al. | 623/20.27 |
| 7,906,064 B2 | 3/2011 | Muratoglu et al. | |
| 7,938,862 B2 * | 5/2011 | Naegerl | 623/20.21 |
| 8,006,839 B2 * | 8/2011 | Hafner | 206/363 |
| 8,066,776 B2 * | 11/2011 | O'Connor et al. | 623/20.32 |
| 8,075,626 B2 * | 12/2011 | Dun | 623/20.27 |
| 8,187,335 B2 * | 5/2012 | Wyss et al. | 623/20.27 |
| 8,206,451 B2 * | 6/2012 | Wyss et al. | 623/20.27 |
| 8,292,965 B2 * | 10/2012 | Walker | 623/20.27 |
| 8,298,288 B2 * | 10/2012 | Walker | 623/20.21 |
| 8,317,869 B2 * | 11/2012 | Cloutier et al. | 623/20.3 |
| 8,317,870 B2 * | 11/2012 | Wagner et al. | 623/20.32 |
| 8,328,874 B2 * | 12/2012 | Lee | 623/20.3 |
| 8,337,564 B2 * | 12/2012 | Shah et al. | 623/20.27 |
| 8,382,847 B2 * | 2/2013 | Wyss et al. | 623/20.27 |
| 8,480,752 B2 * | 7/2013 | Dun | 623/20.33 |
| 8,496,704 B2 * | 7/2013 | Lenz et al. | 623/13.13 |
| 8,535,383 B2 * | 9/2013 | Aram et al. | 623/20.15 |
| 8,568,486 B2 * | 10/2013 | Wentorf et al. | 623/20.32 |
| 8,574,304 B2 * | 11/2013 | Wentorf et al. | 623/20.32 |
| 8,613,775 B2 * | 12/2013 | Wentorf et al. | 623/20.32 |
| 8,636,807 B2 * | 1/2014 | Komistek | 623/20.33 |
| 8,715,360 B2 * | 5/2014 | Samuelson et al. | 623/20.32 |
| 8,721,731 B2 * | 5/2014 | Samuelson et al. | 623/20.32 |
| 2002/0068979 A1 * | 6/2002 | Brown et al. | 623/20.3 |
| 2003/0055509 A1 * | 3/2003 | McCue et al. | 623/20.32 |
| 2004/0006394 A1 * | 1/2004 | Lipman et al. | 623/20.29 |
| 2004/0083005 A1 * | 4/2004 | Jacobsson et al. | 623/23.44 |
| 2004/0138755 A1 * | 7/2004 | O'Connor et al. | 623/20.32 |
| 2005/0055102 A1 * | 3/2005 | Tornier et al. | 623/20.32 |
| 2005/0197710 A1 * | 9/2005 | Naegerl | 623/20.32 |
| 2005/0209703 A1 * | 9/2005 | Fell | 623/20.33 |
| 2006/0100714 A1 * | 5/2006 | Ensign | 623/20.16 |
| 2006/0190087 A1 * | 8/2006 | O'Connor et al. | 623/20.33 |
| 2006/0195195 A1 * | 8/2006 | Burstein et al. | 623/20.33 |
| 2006/0212124 A1 * | 9/2006 | Siebel | 623/20.31 |
| 2006/0265078 A1 * | 11/2006 | McMinn | 623/20.14 |
| 2006/0265080 A1 * | 11/2006 | McMinn | 623/20.27 |
| 2007/0083266 A1 * | 4/2007 | Lang | 623/17.11 |
| 2007/0135926 A1 * | 6/2007 | Walker | 623/20.31 |
| 2007/0299531 A1 * | 12/2007 | Rhodes et al. | 623/20.32 |
| 2007/0299532 A1 * | 12/2007 | Rhodes et al. | 623/20.32 |
| 2008/0215142 A1 | 9/2008 | Muratoglu et al. | |
| 2008/0243259 A1 * | 10/2008 | Lee et al. | 623/20.32 |
| 2009/0043396 A1 * | 2/2009 | Komistek | 623/20.32 |
| 2009/0105364 A1 | 4/2009 | Merrill et al. | |
| 2009/0210066 A1 | 8/2009 | Jasty | |
| 2009/0226068 A1 * | 9/2009 | Fitz et al. | 382/131 |
| 2010/0076562 A1 * | 3/2010 | Fell et al. | 623/20.3 |
| 2010/0131071 A1 * | 5/2010 | O'Connor et al. | 623/20.32 |
| 2010/0190882 A1 | 7/2010 | Muratoglu et al. | |
| 2010/0191341 A1 * | 7/2010 | Byrd | 623/20.3 |
| 2010/0280624 A1 * | 11/2010 | Engh et al. | 623/20.29 |
| 2010/0331848 A1 * | 12/2010 | Smith et al. | 606/88 |
| 2011/0015750 A1 * | 1/2011 | Popoola et al. | 623/20.32 |
| 2011/0029091 A1 * | 2/2011 | Bojarski et al. | 623/20.32 |
| 2011/0137427 A1 | 6/2011 | Otto et al. | |
| 2012/0022658 A1 * | 1/2012 | Wentorf | 623/20.28 |
| 2012/0035736 A1 * | 2/2012 | O'Connor et al. | 623/20.32 |
| 2012/0109324 A1 * | 5/2012 | Keggi et al. | 623/20.21 |
| 2012/0197409 A1 * | 8/2012 | McKinnon et al. | 623/20.27 |
| 2013/0131819 A1 * | 5/2013 | Parisi et al. | 623/20.33 |
| 2013/0204383 A1 * | 8/2013 | Wentorf | 623/20.32 |
| 2013/0218283 A1 * | 8/2013 | Samuelson et al. | 623/20.29 |
| 2013/0317619 A1 * | 11/2013 | Goodfellow et al. | 623/20.3 |
| 2013/0317620 A1 * | 11/2013 | Lenz et al. | 623/20.15 |
| 2013/0317621 A1 * | 11/2013 | Metzger et al. | 623/20.31 |
| 2014/0025175 A1 * | 1/2014 | Wentorf et al. | 623/20.32 |
| 2014/0025176 A1 * | 1/2014 | Wentorf et al. | 623/20.32 |
| 2014/0025177 A1 * | 1/2014 | Wentorf et al. | 623/20.32 |
| 2014/0052268 A1 * | 2/2014 | Sanford et al. | 623/20.32 |
| 2014/0107793 A1 * | 4/2014 | Komistek | 623/20.23 |
| 2014/0156015 A1 * | 6/2014 | Parisi et al. | 623/20.29 |
| 2014/0163687 A1 * | 6/2014 | Parisi et al. | 623/20.33 |

OTHER PUBLICATIONS

Banks et al., Comparing in vivo kinematics of unicondylar and bi-unicondylar knee replacements. Knee Surg Sports Traumatol Arthrosc. Oct. 2005;13(7):551-6. Epub Jan. 20, 2005.

Johal et al., Tibio-femoral movement in the living knee. A study of weight bearing and non-weight bearing knee kinematics using 'interventional' MRI. J Biomech. Feb. 2005;38(2):269-76.

Komistek et al., In vivo fluoroscopic analysis of the normal human knee. Clin Orthop Relat Res. May 2003;(410):69-81.

Moro-oka et al., Dynamic activity dependence of in vivo normal knee kinematics. J Orthop Res. Apr. 2008;26(4):428-34.

Most et al., Femoral rollback after cruciate-retaining and stabilizing total knee arthroplasty. Clin Orthop Relat Res. May 2003;(410):101-13.

Yue et al., Kinematics of medial osteoarthritic knees before and after posterior cruciate ligament retaining total knee arthroplasty. J Orthop Res. Jan. 2011;29(1):40-6. doi: 10.1002/jor.21203.

* cited by examiner

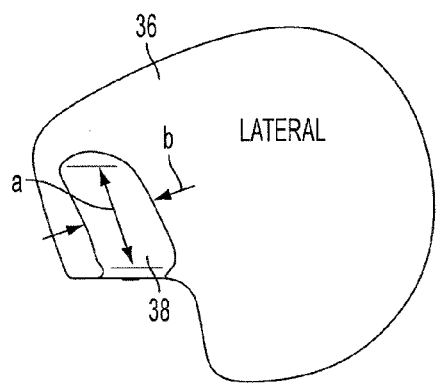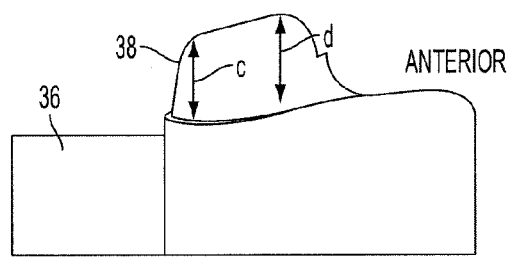
FIG. 6    FIG. 7
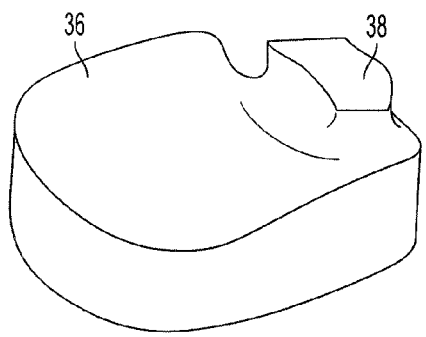
FIG. 8

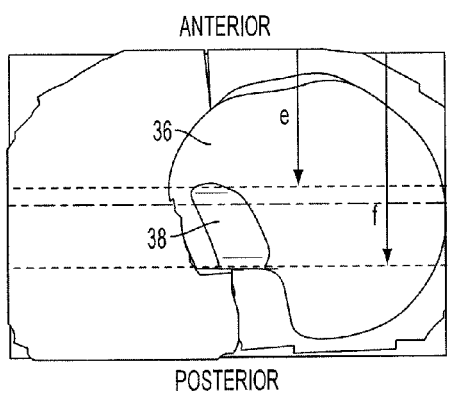
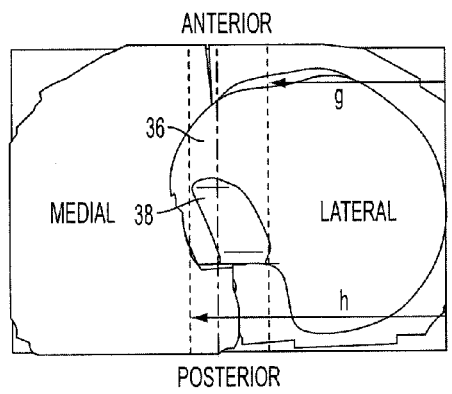
FIG. 9     FIG. 10
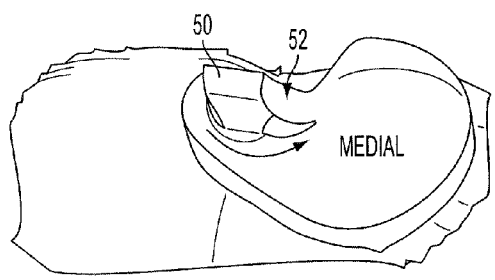
FIG. 11

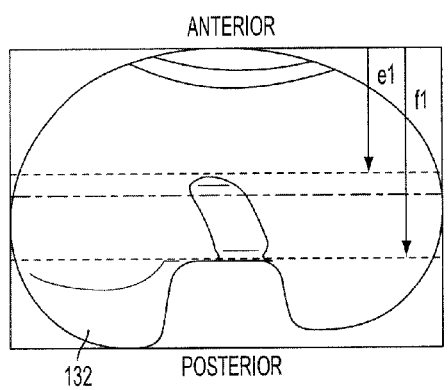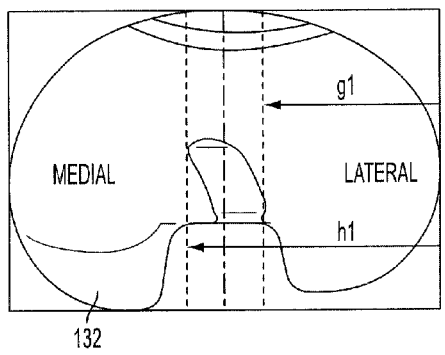
FIG. 42    FIG. 43
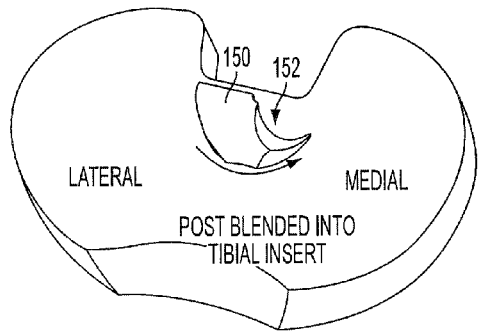
FIG. 44

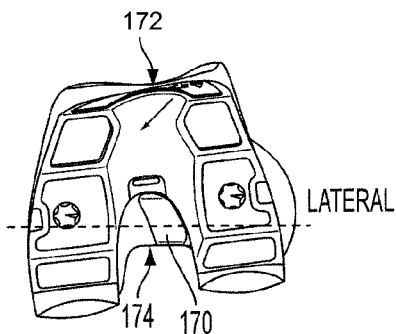
FIG. 47
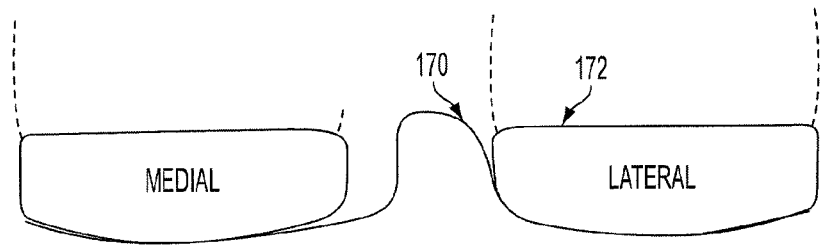
FIG. 48
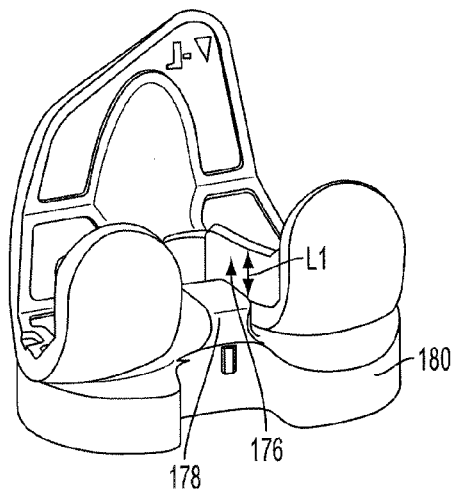 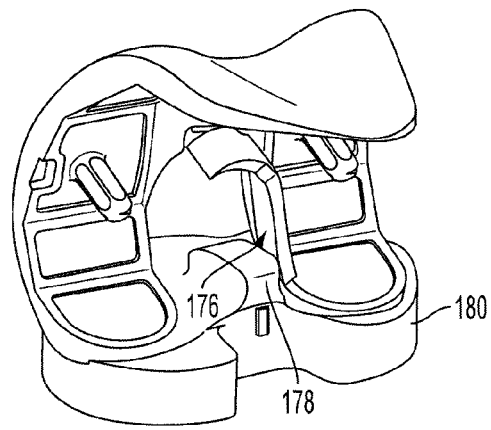
FIG. 49  FIG. 50

METHODS AND DEVICES FOR KNEE JOINT REPLACEMENT WITH ANTERIOR CRUCIATE LIGAMENT SUBSTITUTION

CROSS REFERENCES

The present application claims priority to U.S. Provisional Patent Application No. 61/507,434 entitled "Methods and Devices for Knee Joint Replacement with Anterior Cruciate Ligament Substitution" filed Jul. 13, 2011, which is hereby incorporated by reference in its entirety.

FIELD OF THE INVENTION

The present invention relates to methods and devices for knee joint replacement with anterior cruciate ligament (ACL) substitution, and in particular to methods and devices for substituting a prosthesis for an ACL.

BACKGROUND OF THE INVENTION

FIG. 1 illustrates a typical knee joint including a femur 1 and a tibia 3, shown with healthy femur cartilage 5 and healthy tibia cartilage 7. The knee joint includes three primary elements: a medial tibiofemoral joint, a lateral tibiofemoral joint, and a central patellofemoral joint. Joint trauma or diseases such as osteoarthritis and rheumatoid arthritis can cause severe damage to one or more of these elements. In a case where one or more of the knee elements are traumatized or diseased, while the other one or two knee elements are healthy, the traumatized or diseased element(s) can be replaced in a partial knee replacement surgical procedure. In a case where all three primary elements are traumatized or diseased, all three elements can be replaced in a total knee replacement surgical procedure.

In both partial and total knee replacement surgical procedures, the traumatized or diseased ones of the knee's bony surfaces, e.g., femur, tibia, and patella, can be replaced by prosthetic components. The knee's soft-tissue structures, particularly ligaments surrounding the knee joint, can be largely left intact. The knee's major ligament structures include medial and lateral collateral structures, and anterior and posterior cruciate ligaments. These ligamentous structures play a significant role in controlling the motion and stability of a knee joint. With regards to the cruciate ligaments, the posterior cruciate ligament (PCL) is generally present and well-functioning in patients undergoing partial or total knee replacement surgery. However, in at least some patients, the anterior cruciate ligament (ACL) can be absent or non-functional at surgery due to prior trauma or gradual degradation.

Traditional partial knee replacement prostheses have no mechanism for substitution of ACL function. Consequently, patients with an absent or non-functional ACL may end up receiving total joint replacement, which is a generally more invasive procedure than partial knee replacement and which replaces the healthy element(s) of the patient's knee. Alternatively, instead of total knee replacement, patients with an absent or non-functional ACL may undergo additional surgery prior to a partial knee replacement surgical procedure to reconstruct the ACL, such as with a soft tissue graft.

In traditional total knee replacement surgical procedures, patients receive a type of prosthesis, e.g., a cruciate retaining (CR) type implant, that allows the present and well-functioning PCL to be retained. However, even for patients who have a functional ACL, the ACL is traditionally resected during surgery prior to implantation of a CR type implant because of difficulty in achieving optimal soft-tissue balancing and component placement with both the ACL and PCL present. However, traditional CR prostheses have no mechanism for substitution of the ACL function. Consequently, following CR prosthesis implantation, the knee shows abnormal motion patterns characterized by features such as reduced tibial internal rotation and paradoxical anterior femoral translation.

Accordingly, there remains a need for improved knee prostheses and methods for treating disease and trauma affecting the knee.

SUMMARY OF THE INVENTION

The present invention generally provides methods and devices for knee joint replacement with anterior cruciate ligament (ACL) substitution. In one aspect, a medical device is provided that includes a tibial implant, a femoral implant, and a post. The tibial implant has an inferior surface and an opposite, superior surface. The inferior surface is configured to be fixed to a tibia of a patient. The femoral implant is mateable to the tibial implant and has an inferior surface and an opposite, superior surface. The superior surface of the femoral implant is configured to be fixed to a femur of the patient, and the tibial implant is configured to articulate relative to the femoral implant when the tibial implant is fixed to the tibia and the femoral implant is fixed to the femur. The post extends from the superior surface of the tibial implant near an edge thereof. The post is configured to be substantially centered on the tibia when the tibial implant is fixed thereto such that the post simulates an ACL when the tibial implant is fixed to the tibia and the femoral implant is fixed to the femur.

The tibial implant can have a variety of configurations. The tibial implant can have a medial compartment configured to be seated on a medial surface of the tibia with a first portion of the tibial implant being seated on or over the tibia's medial surface and a second, substantially smaller portion of the tibial implant being seated on or over the tibia's lateral surface. The tibial implant can have a lateral compartment configured to be seated on a lateral surface of the tibia with a first portion of the tibial implant being seated on or over the tibia's lateral surface and a second, substantially smaller portion of the tibial implant being seated on or over the tibia's medial surface. The tibial implant can have medial and lateral compartments. The lateral compartment can be configured to be seated on a lateral surface of the tibia such that the lateral surface is substantially covered by the lateral compartment. The medial compartment can be configured to be seated on a medial surface of the tibia such that the medial surface is substantially covered by the medial compartment.

The post can have a variety of configurations. The post can be asymmetric in sagittal, coronal, and transverse planes. The post can be integrally formed with the tibial implant, or the post can be a discrete element configured to couple to the tibial implant.

In some embodiments, the device can include a femoral notch structure coupled to the femoral implant. The femoral notch structure can be configured to prevent the post from impinging on a lateral surface of the femur through a full range of knee flexion when the tibial implant is fixed to the tibia and the femoral implant is fixed to the femur. The post can be configured to articulate relative to the femoral notch structure.

In another aspect, a medical method is provided that includes implanting a partial knee prosthesis in a patient to replace one of a medial tibiofemoral joint of a knee and a lateral tibiofemoral joint of the knee such that an inferior surface of a tibial implant of the knee prosthesis faces a tibia of the knee, a superior surface of the tibial implant faces an inferior surface of a femoral implant of the knee prosthesis, a superior surface of the femoral implant faces a femur of the knee, and a post extending from the superior surface of the tibial implant functions as a substitute for an ACL of the knee. The tibial implant and the post are configured to articulate relative to the femoral implant, and the post does not impinge on a lateral surface of the femur when the post articulates relative to the femoral implant through a full range of knee flexion.

In another embodiment, a medical method is provided that includes implanting a total knee prosthesis in a patient to replace both of a medial tibiofemoral joint of a knee and a lateral tibiofemoral joint of the knee such that an inferior surface of a tibial implant of the knee prosthesis faces a tibia of the knee, a superior surface of the tibial implant faces an inferior surface of a femoral implant of the knee prosthesis, a superior surface of the femoral implant faces a femur of the knee, and a post extending from the superior surface of the tibial implant functions as a substitute for an ACL of the knee. The tibial implant and the post are configured to articulate relative to the femoral implant, and the post does not impinge on a lateral surface of the femur when the post articulates relative to the femoral implant through a full range of knee flexion.

BRIEF DESCRIPTION OF THE DRAWINGS

The invention will be more fully understood from the following detailed description taken in conjunction with the accompanying drawings, in which:

FIG. 6 is a top view of a tibial insert of the lateral knee prosthesis of FIG. 3;

FIG. 7 is a side view of the tibial insert of FIG. 6;

FIG. 8 is a perspective view of the tibial insert of FIG. 6;

FIG. 9 is a top view of the tibial insert of the lateral knee prosthesis of FIG. 3 seated on the tibia;

FIG. 10 is another top view of the tibial insert of FIG. 9;

FIG. 11 is a perspective view of one embodiment of a medial knee prosthesis attached to a tibia, the medial knee prosthesis including a post gradually blending into a tibial insert of the prosthesis;

FIG. 42 is a top view of the tibial implant of FIG. 39;

FIG. 43 is another top view of the tibial implant of FIG. 39;

FIG. 44 is a perspective view of one embodiment of a total knee replacement prosthesis including a post gradually blending into a tibial insert of the prosthesis;

FIG. 47 is a top view of one embodiment of a total knee replacement prosthesis including a post having a rounded top;

FIG. 48 is a side schematic view of the prosthesis of FIG. 47;

FIG. 49 is a perspective view of one embodiment of a total knee replacement prosthesis in an extended or closed position;

FIG. 50 is a perspective view of the prosthesis of FIG. 49 in a flexed or open position;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for knee joint replacement with anterior cruciate ligament (ACL) substitution. In general, the methods and devices can allow a knee joint to be partially or totally replaced in conjunction with substitution of the knee joint's ACL. In other words, when an ACL is absent, non-functional, or otherwise needs repair during a partial or total knee replacement surgical procedure, a partial or total knee replacement prosthesis can be implanted in the same surgical procedure as an ACL substitute. Providing a substitute for an ACL with a knee replacement prosthesis can help reduce a number of surgical procedures needed to repair the knee and/or can help the knee's functionality approach 100% after surgery.

The prostheses described herein can be formed of one or more materials, such as polyolefins, polyethylene, ultra-high molecular weight polyethylene, medium-density polyethylene, high-density polyethylene, medium-density polyethylene, highly crosslinked ultra-high molecular weight polyethylene (UHMWPE), etc. Exemplary embodiments of UHMWPE prosthesis materials and manufacturing processes are described in U.S. application Ser. No. 08/600,744 (now U.S. Pat. No. 5,879,400) filed Feb. 13, 1996, entitled "Melt-Irradiated Ultra High Molecular Weight Polyethylene Prosthetic Devices;" U.S. application Ser. No. 12/333,572 filed Dec. 12, 2008, entitled "Radiation And Melt Treated Ultra High Molecular Weight Polyethylene Prosthetic Devices;" U.S. application Ser. No. 11/564,594 (now U.S. Pat. No. 7,906,064) filed Nov. 29, 2006, entitled "Methods For Making Oxidation Resistant Polymeric Material;" U.S. application Ser. No. 12/522,728 filed Apr. 5, 2010, entitled "Methods For Making Oxidation-Resistant Cross-Linked Polymeric Materials;" U.S. application Ser. No. 11/030,115 (now U.S. Pat. No. 7,166,650) filed Jan. 7, 2005, entitled "High Modulus Crosslinked Polyethylene With Reduced Residual Free Radical Concentration Prepared Below The Melt;" U.S. application Ser. No. 12/041,249 filed Mar. 3, 2008, entitled "Cross-Linking Of Antioxidant-Containing Polymers;" which are hereby incorporated by reference in their entireties.

Figure 1:
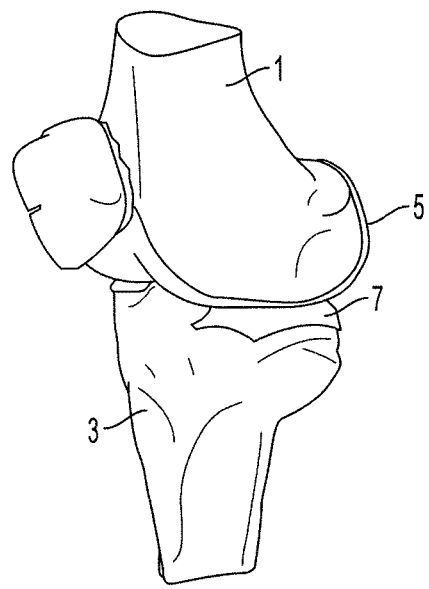
FIG. 1 (PRIOR ART) is a perspective view of a typical normal human knee.
Figure 1A:
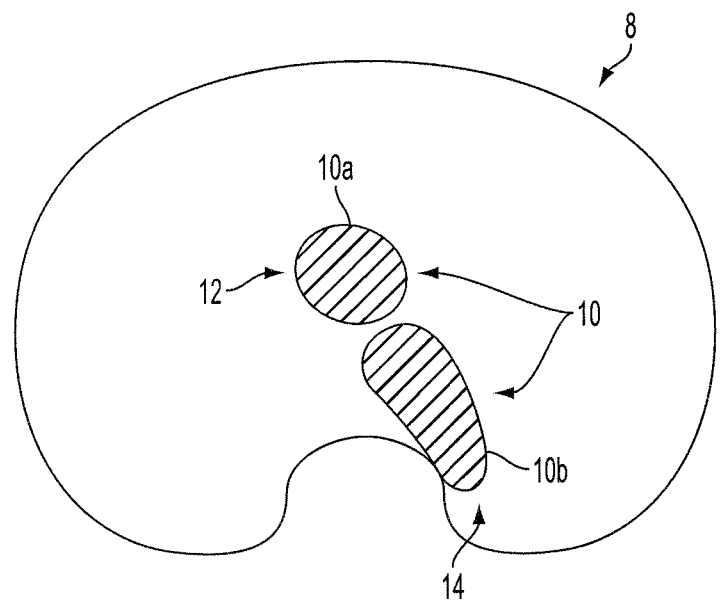
FIG. 1A is view of one embodiment of a knee prosthesis having an ACL-substitution member including a plurality of discrete pieces.

Generally, a knee replacement prosthesis, also referred to herein as a "knee replacement prosthesis," a "prosthesis," and an "implant," can include a medial or lateral femoral component, also referred to herein as a "femoral implant," a femoral intercondylar notch structure, a medial or lateral tibial insert, also referred to herein as a "tibial implant," and an ACL-substitution member, also referred to herein as an "ACL-substitution member," "ACL-substituting post," a "tibial post," and a "post." The femoral intercondylar notch structure can be formed integrally with the femoral component, or the femoral intercondylar notch structure can be a discrete element from the femoral component. The ACL-substitution member can be configured to engage with the femoral intercondylar notch structure, also referred to herein as a "femoral intercondylar notch structure" and a "femoral notch structure." The ACL-substitution member can extend from a surface of the tibial insert, such as by being an integral part thereof, by being integrally formed with another portion of the prosthesis, or by being a discrete element configured to couple to the tibial insert. In an exemplary embodiment, the ACL-substitution member can be integrally formed with a tibial baseplate of the prosthesis. In other exemplary embodiments, the ACL-substitution member can be integrally formed with the tibial insert and extend from a tibial articular surface thereof. The ACL-substitution member can be a unitary or singular element, or it can include a plurality of discrete pieces. FIG. 1A illustrates an exemplary embodiment of a prosthesis 8 having an ACL-substitution member 10 including multiple pieces, e.g., an anterior piece 10a and a lateral piece 10b, configured to engage with corresponding regions of the femoral notch. For reference, a top side of FIG. 1A is an anterior side of the prosthesis 8, and a right side of FIG. 1A is a lateral side of the prosthesis 8. Thus, an anterior part 12 of the anterior piece 10a is on a left side of FIG. 1A, and a posterior lateral part 14 of the lateral piece 10b is on a bottom side of FIG. 1A. Exemplary embodiments of articular surface geometry are described in Intl. App. No. PCT/US2010/059387 filed Dec. 8, 2010, entitled "Implant For Restoring Normal Range Of Flexion And Kinematics Of The Knee," which is hereby incorporated by reference in its entirety.

Figure 1B:
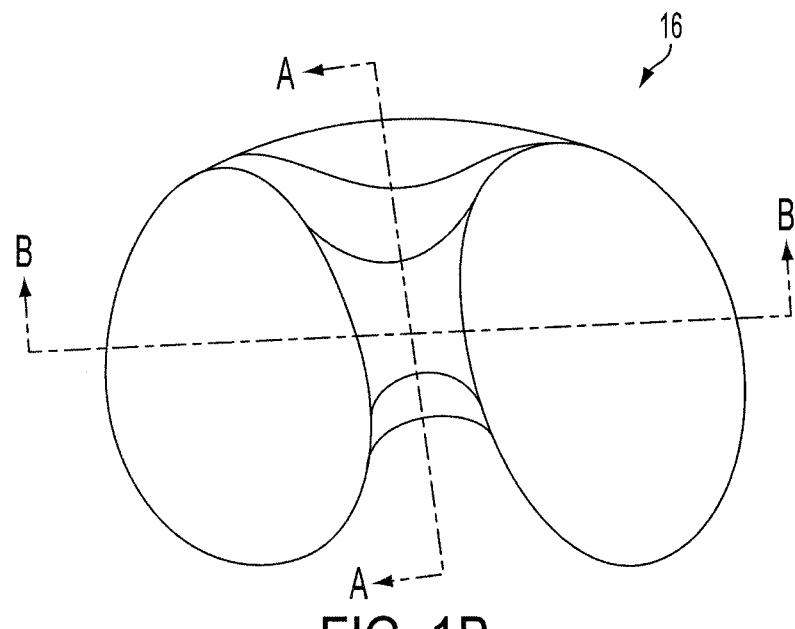
FIG. 1B is a top view of one embodiment of a knee prosthesis.
Figure 1C:
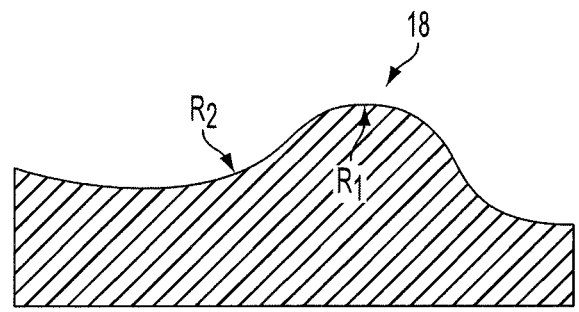
FIG. 1C is a sagittal cross-sectional view of the knee prosthesis of FIG. 1B.
Figure 1D:
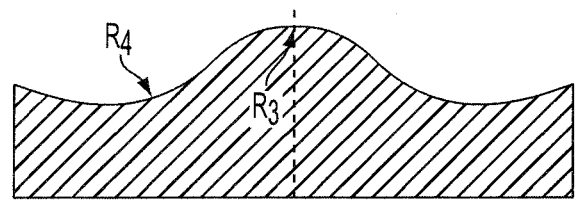
FIG. 1D is a coronal cross-sectional view of the knee prosthesis of FIG. 1B.

Embodiments of prostheses described herein can generally be configured to substitute the function of an ACL via engagement of the femoral intercondylar notch with the prosthesis, e.g., with the ACL-substitution member of the prosthesis, during a full range of knee motion, e.g., in a range of about −20° to 160° knee flexion, and/or during only early knee flexion, e.g., in a range of about −20° to 40°. In an exemplary embodiment, the ACL-substitution member configured to engage the femoral intercondylar notch can have a low profile, e.g., be a short post. In another embodiment of a prosthesis 16, shown in FIGS. 1B, 1C, and 1D, an ACL-substitution member configured to engage the femoral intercondylar notch can include a two-step eminence between the medial and lateral tibial plateau that blends smoothly with the medial and lateral articular surfaces in the coronal and sagittal planes. Radii R1, R2, R3, R4 of the prosthesis 16 can be in a range of about 2 to 100 mm, e.g., about 2 to 30 mm, about 5 to 25 mm, about 12 to 20 mm, about 25 to 50 mm, about 55 to 95 mm, etc. The radii R1 and R3 are at a tibial eminence of the prosthesis 16, e.g., at an ACL-substitution member 18 of the prosthesis 16. In an exemplary embodiment, the radii R1 and R3 can each be about 10 mm, and the radii R2 and R4 can each be about 5 mm.

Figure 1E:
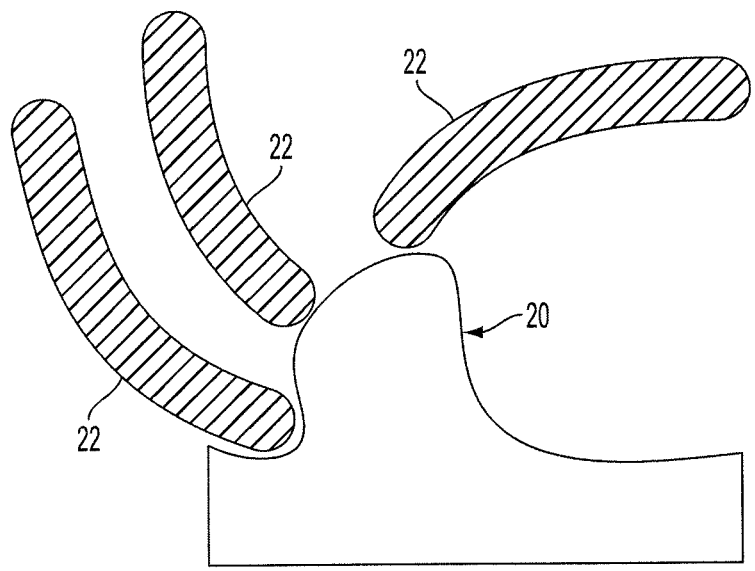
FIG. 1E is a side view of one embodiment of a knee prosthesis including an ACL-substitution member and a femoral notch structure configured to engage through a full range of knee motion.
Figure 1F:
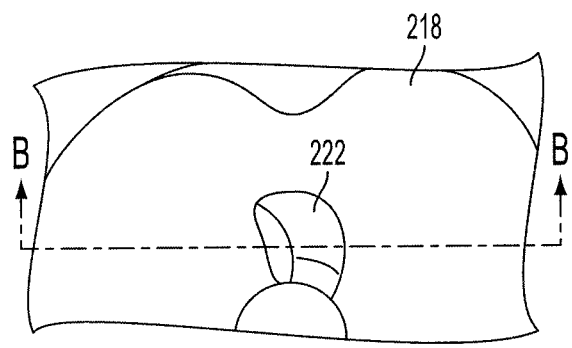
FIG. 1F is top, partial view of one embodiment of a tibial insert.
Figure 1G:
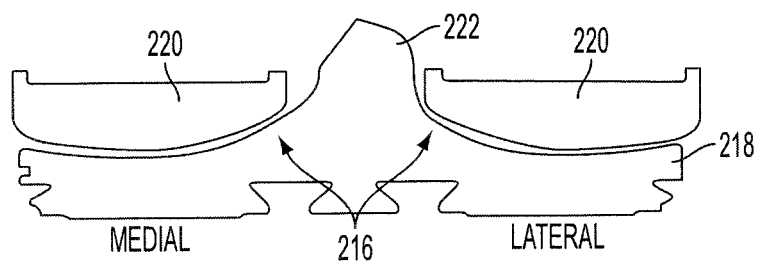
FIG. 1G is coronal section view B-B of the tibial insert of FIG. 1F and a femoral implant.

In another embodiment, a prosthesis can be configured to restrict mediolateral motion of the prosthesis's femoral component, which can prevent impinging a PCL between the femoral component and the prosthesis's tibial post and can prevent impinging the tibial post against femoral bone. An exemplary embodiment of such a prosthesis is illustrated in FIGS. 1F and 1G in which a central eminence portion 216 of a tibial articular surface adjacent a post 222 of a tibial insert 218 substantially conforms to a surface of a femoral implant 220 mateable to the tibial insert 218. This substantial conformity can restrict mediolateral motion of the femoral implant 220 and thereby prevent impingement of a PCL and/or femoral bone against the post 222.

Embodiments of prostheses described herein can be configured to be fixed to a patient's tibia, which can facilitate healing and/or functionality of the prosthesis. In one embodiment, the prosthesis can be configured to be directly fixed to a tibia using bone cement. As will be appreciated by a person skilled in the art, any bone cement can be used to so affix the prosthesis. In another embodiment, the prosthesis can be nonremovably coupled to a base, e.g., a biocompatible metallic base. The metal base can be configured to be fixed to a tibia by using bone cement and/or by bone ingrowth or ongrowth at the bone/base interface. In yet another embodiment, the prosthesis can be molded into a base, e.g., a biocompatible metallic base, by forming a monoblock implant. In still another embodiment, the prosthesis can be removably coupled to a base, e.g., a biocompatible metallic base using a locking mechanism. The locking mechanism can be configured to be actuated to affix the prosthesis to the base either during manufacture or intraoperatively during surgery.

In use, with the prosthesis implanted in a patient, during knee flexion from an extended position, the ACL-substitution member can be configured to engage with the femoral notch structure, which can prevent the patient's femur from displacing posteriorly, and can gradually guide the femur's external rotation. In an exemplary embodiment, during knee flexion from an extended position, anterior and lateral edges of the ACL-substitution member can be configured to engage with anterior and lateral edges of the femoral notch structure. With the prosthesis implanted in the patient, during terminal extension from a flexed position, the ACL-substitution member can be configured to engage with the femoral notch structure, which can pull the patient's femur forward, and can gradually guide the femur's internal rotation. Generally, as illustrated in an embodiment shown in FIG. 1E, an ACL-substitution member 20 and a femoral notch structure 22 can be configured to engage through the full range of knee motion. The femoral notch structure 22 is shown in cross-section in FIG. 1E at different flexion angles. In an exemplary embodiment, this engagement can occur during only early knee flexion, e.g., in a range of about −20° to 40°. In this way, the ACL-substitution member and the femoral notch engagement can be configured to substitute for an absent, non-functional, or otherwise damaged ACL ligament. The knee replacement prosthesis can also be configured to accommodate a patient's PCL. Because a patient's PCL can be generally present and well-functioning in patients undergoing partial or total knee replacement surgery, the prosthesis can be implanted in the patient while allowing the patient's PCL to remain and be functional in the patient's body.

Knee replacement prostheses described herein can be configured to be used in partial knee replacement surgical procedures and in total knee replacement surgical procedures. Exemplary embodiments of prostheses for both types of procedures are discussed in turn below.

Figure 2:
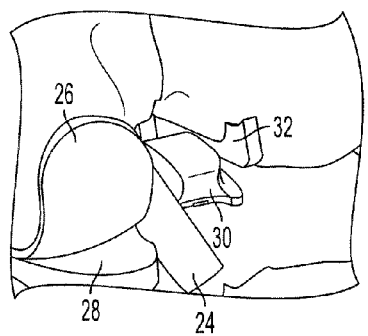
FIG. 2 is a posterior perspective view of one embodiment of a medial knee prosthesis attached to a tibia and a femur.
Figure 3:
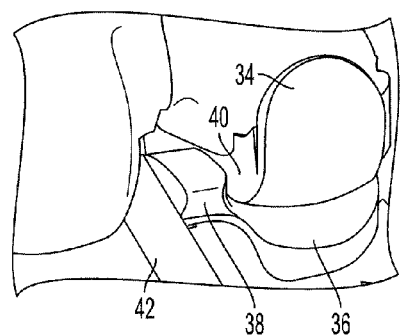
FIG. 3 is a posterior perspective view of one embodiment of a lateral knee prosthesis attached to a tibia and a femur.

FIG. 2 illustrates an exemplary embodiment of a knee replacement prosthesis configured to provide substitution of an ACL in partial knee replacement surgery. The prosthesis of FIG. 2 is a medial femoral prosthesis configured to resurface a medial tibial compartment. In FIG. 2 showing the prosthesis implanted in a patient, the patient's PCL ligament 24 is represented as a cylinder joining the tibial insertion of the ligament 24 to its insertion on the medial femoral condyle within the intercondylar region. As in the illustrated embodiment, the prosthesis can include a femoral implant 26, a tibial implant 28, an ACL-substituting post 30, and a femoral notch structure 32. The prosthesis shown in FIG. 2 is a medial prosthesis, but a lateral prosthesis can be configured similarly to the prosthesis of FIG. 2. Further, any medial prosthesis described herein can be similarly configured as a lateral prosthesis, and vice versa. FIG. 3 illustrates an exemplary embodiment of a lateral knee replacement prosthesis including a femoral implant 34, a tibial implant 36, an ACL-substituting post 38, and a femoral notch structure 40 configured to provide substitution of an ACL in partial knee replacement surgery and to resurface a lateral tibial compartment. FIG. 3 also represents the patient's PCL ligament 42 as a cylinder.

The tibial implant 36 can have a variety of configurations. Although in the illustrated embodiment the post 38 is integrally formed with the tibial implant 36, in some embodiments, the post 38 and the tibial implant 36 can be discrete elements. If the post and the tibial implant are discrete elements, in any of the embodiments described herein, the post can be configured to removably and replaceably couple to the tibial implant. In this way, a kit can be provided including a plurality of different posts, e.g., posts having different sizes, being formed from different materials, etc., and a tibial implant configured to couple to each of the different posts. Similarly, a kit can be provided including a plurality of different tibial implants and one post, or a plurality of different posts, the one post or each of the plurality of posts being configured to couple to any one of the tibial implants.

Generally, a medial tibial implant can be configured as a substitute for a medial tibiofemoral joint. As in the embodiment illustrated in FIGS. 2, 4, and 5, the tibial implant 28 can have a shape substantially conforming to a shape of a medial tibial compartment, e.g., a medial surface of a tibia 29. The tibial implant 28 can have a size, e.g., a surface area configured to face the medial tibial compartment, substantially similar to the medial tibial compartment such that the tibial implant 28 can be seated on the medial tibial compartment without extending beyond outside edges of the tibia 29 except for a portion extending over a portion of a lateral tibial compartment, e.g., a lateral surface of the tibia 29. In other words, the tibial implant 28 can have a size and shape such that the tibial implant 28 can be seated on the tibia 29 with a first portion of the tibial implant 28 being seated on or over the tibia's medial surface and a second, substantially smaller portion of the tibial implant being seated on or over the tibia's lateral surface.

Figure 4:
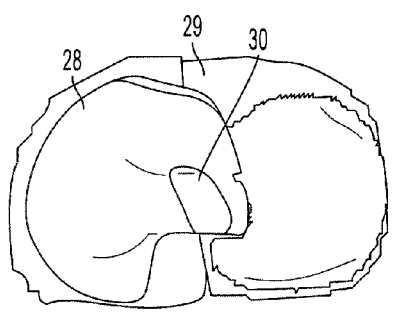
FIG. 4 is a top view of a tibial insert of the medial knee prosthesis of FIG. 2 seated on the tibia.
Figure 5:
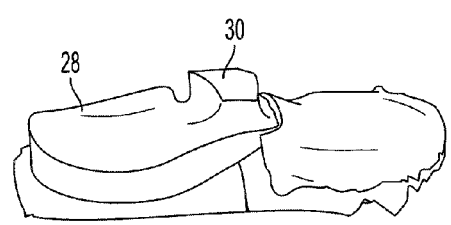
FIG. 5 is a side perspective view of the tibial insert of FIG. 4.

The tibial implant 28 can have the post 30 coupled thereto near an edge thereof such that the post 30 can be positioned at a region near a center of the proximal tibial bone, as also illustrated in FIGS. 4 and 5, such that the post 30 can occupy a lateral portion of the intercondylar region. The post 30 coupled to the tibial implant 28 can have a variety of configurations. As in the illustrated embodiment, the post 30 can be asymmetric in sagittal, coronal, and transverse planes. For non-limiting example, with reference to the embodiment of the lateral prosthesis illustrated in FIG. 3, the tibial implant 36 of which having the post 38 integrally formed therewith is also illustrated in FIGS. 6-8, 9, and 10, the post 38 can have an anteroposterior length a in a range of about 5 to 35 mm, e.g., in a range of about 10 to 20 mm, about 15 mm, etc. The prosthesis's post can have a mediolateral width b of in a range of about 5 to 25 mm, e.g., in a range of about 5 to 20 mm, in a range of about 5 to 15 mm, in a range of about 8 to 15 mm, about 9 mm, etc. The post 38 can have a posterior height c in a range of about 1 to 25 mm, e.g., in a range of about 5 to 20 mm, in a range of about 5 to 15 mm, about 8 mm, etc. The post 38 can have an anterior height d in a range of about 3 to 25 mm, e.g., in a range of about 5 to 20 mm, in a range of about 8 to 15 mm, about 10 mm, etc. In some embodiments, the post's anterior post height can be less than or equal to the post's posterior post height. The post 38 can have a posterior slope in the sagittal view such that its height anteriorly, e.g., in a range of about 8 to 15 mm, can be higher than its height posteriorly, e.g., in a range of about 5 to 10 mm.

The location of the post 38 relative to the tibial insert 36 can vary. For non-limiting example, with reference to the embodiment of the lateral prosthesis illustrated in FIGS. 9 and 10, a distance e from an anterior edge of the post to an anterior edge of the tibial base can be in a range of about 5 to 40 mm, e.g., in a range of about 10 to 30 mm, in a range of about 15 to 25 mm, about 22 mm, etc. A distance f from a posterior edge of the post 38 to the anterior edge of the tibial base can be in a range of about 5 to 60 mm, e.g., in a range of about 15 to 45 mm, in a range of about 30 to 40 mm, about 37 mm, etc. A distance g from a lateral edge of the post 38 to the lateral edge of the tibial base can be in a range of about 10 to 50 mm, e.g., in a range of about 15 to 45 mm, in a range of about 25 to 35 mm, about 30 mm, etc. A distance h from a medial edge of the post 38 to the lateral edge of the tibial base can be in a range of about 15 to 60 mm, e.g., in a range of about 25 to 50 mm, in a range of about 35 to 45 mm, about 43 mm, etc.

Figure 8A:
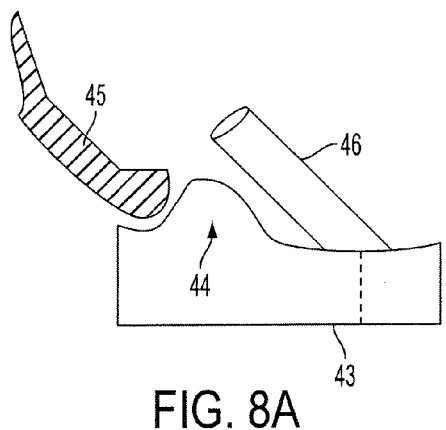
FIG. 8A is a side view of one embodiment of a knee prosthesis including a tibial post located substantially anterior to tibial center.
Figure 8B:
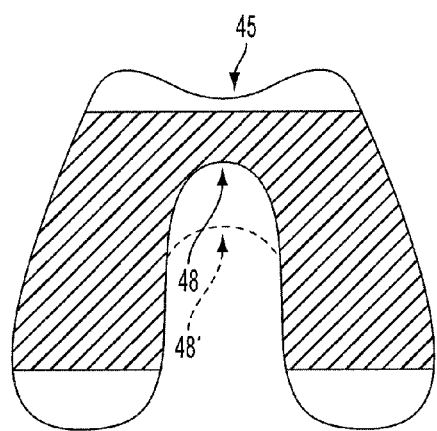
FIG. 8B is top view of the femoral component of the prosthesis of FIG. 8A.
Figure 8C:
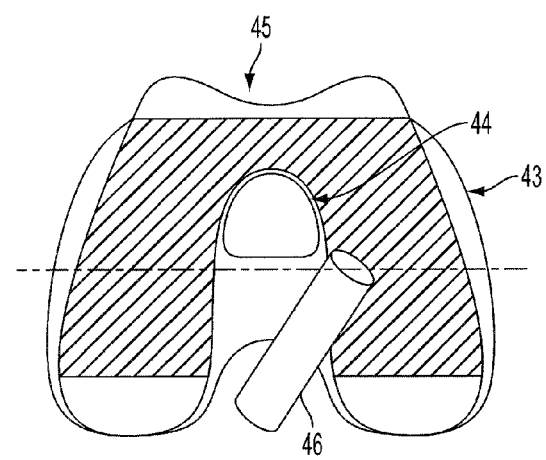
FIG. 8C is a top view of the prosthesis of FIG. 8A.

In another exemplary embodiment, as illustrated in FIGS. 8A, 8B, and 8C, a tibial post 44 of a tibial insert 43 can be located substantially anterior to the tibial center, which can avoid potential impingement of the post 44 with a PCL ligament 46, which is illustrated as a cylinder in FIGS. 8A and 8C. Optionally, as illustrated in FIG. 8B, which shows a femoral component 45 of the prosthesis 43, a femoral intercondylar notch 48 can be extended anteriorly to enable engagement of the femoral notch 48 with the anteriorly located tibial post 44. A dotted line in FIG. 8B illustrates a conventional femoral intercondylar notch 48'.

In another exemplary embodiment, a tibial post can gradually blend into a tibial insert, which can improve strength of the post. FIG. 11 illustrates an exemplary embodiment of a prosthesis including a gradually blending tibial post 50 adjacent a space 52 for a PCL.

Figure 12:
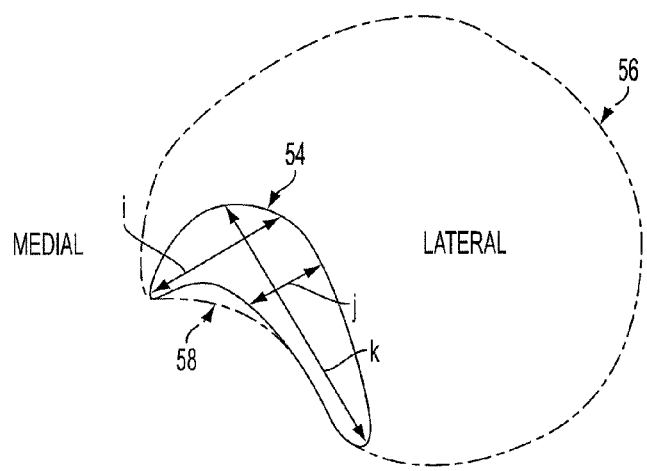
FIG. 12 is a schematic view of one embodiment of a lateral knee prosthesis including a tibial post and a tibial insert, the tibial post having a lateral edge extending back to a posterior edge of the tibial insert.

In yet another exemplary embodiment, a lateral edge of a post can be extended back to a posterior edge of a tibial insert, which can increase tibial post strength. This embodiment can allow gradual tibial post-femoral notch engagement from full flexion to extension, e.g., 155° to −20°, e.g., about 160°, and gradual disengagement from extension to flexion, e.g., −20° to 155°, e.g., about 160°. FIG. 12 illustrates an exemplary embodiment of a prosthesis including a tibial insert having such an extending post 54. In an exemplary embodiment, an anterior width i of the post 54 can be in a range of about 3 to 25 mm, e.g., in a range of about 10 to 20 mm, about 15 mm, etc.; a central width j of the post 54 can be in a range of about 3 to 25 mm, e.g., in a range of about 5 to 15 mm, about 8 mm, etc.; and a length k of the post 54 can be in a range of about 5 to 35 mm, e.g., in a range of about 15 to 30 mm, about 28 mm, etc. FIG. 12 shows a base profile 56 of the tibial insert by dotted outline, with a space 58 for a PCL (not shown) being located adjacent the post 54.

Figure 13:
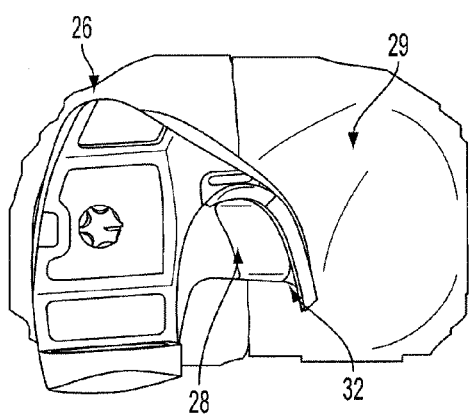
FIG. 13 is a top view of the medial knee prosthesis of FIG. 2 attached to the tibia.
Figure 14:
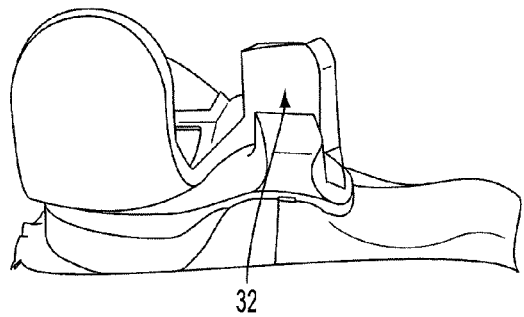
FIG. 14 is a side perspective view of the medial knee prosthesis of FIG. 13.
Figure 13A:
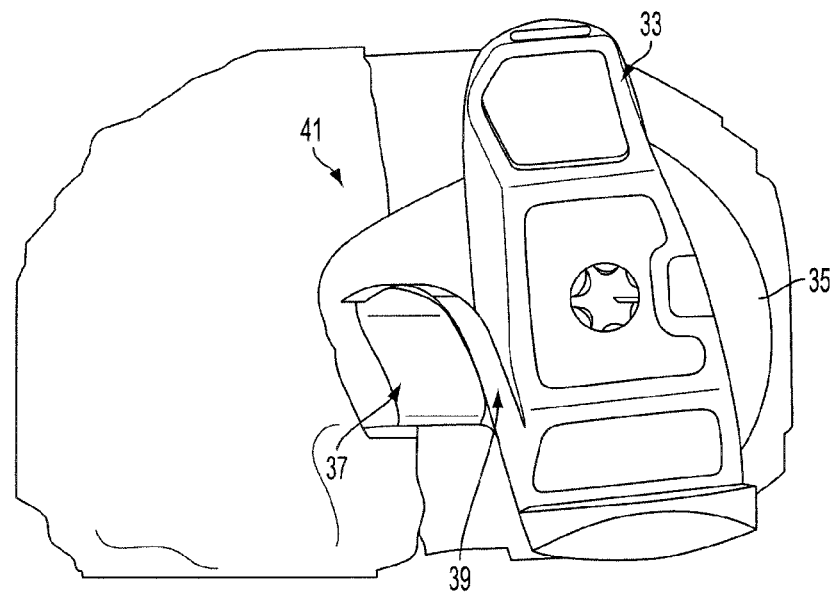
FIG. 13A is a top view of an embodiment of a lateral knee prosthesis attached to a tibia.
Figure 14A:
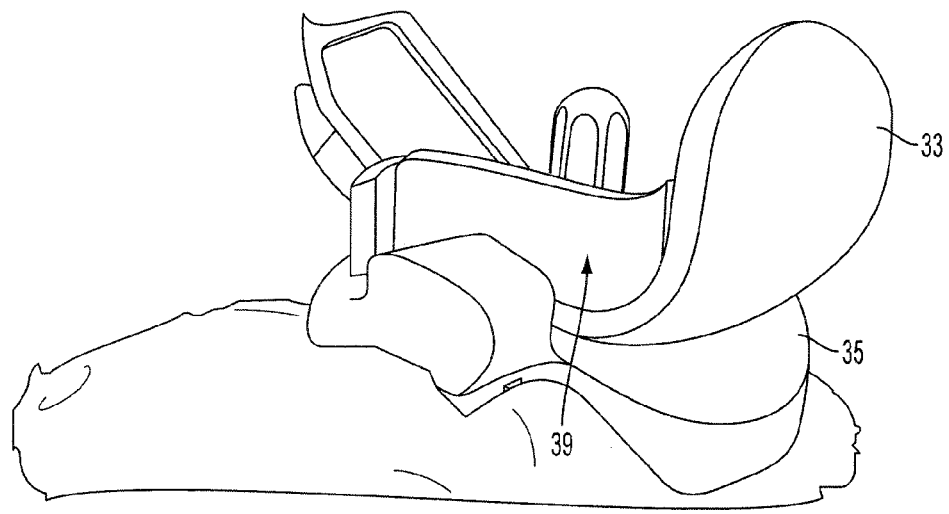
FIG. 14A is a side perspective view of the lateral knee prosthesis of FIG. 13A.

Referring again to the embodiment of FIG. 2, the femoral implant 26 and the femoral notch structure 32, also shown in FIGS. 13 and 14, can also have a variety of configurations. The tibial implant 28 can articulate against, e.g., relative to, the femoral implant 26, and the ACL-substituting tibial post 30 can articulate against the femoral notch structure 32. The prosthesis shown in FIGS. 2, 13, and 14 is a medial prosthesis, but similar to that mentioned above, a lateral prosthesis, such as an embodiment shown in FIGS. 13A and 14A, can be configured similarly to the prosthesis of FIGS. 2, 13, and 14. FIGS. 13A and 14A illustrate an exemplary embodiment of a lateral knee replacement prosthesis including a femoral implant 33, a tibial implant 35 attached to a tibia bone 41, an ACL-substituting post 37, and a femoral notch structure 39.

Figure 15:
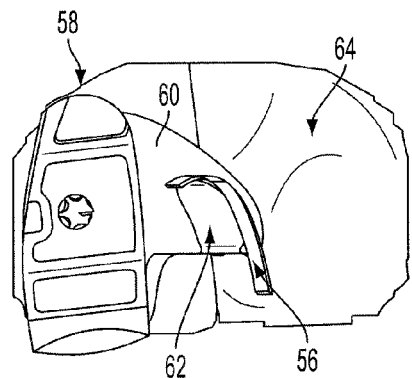
FIG. 15 is a top view of one embodiment of a medial knee prosthesis attached to a tibia, the prosthesis including a discrete femoral notch structure and a discrete femoral implant.
Figure 16:
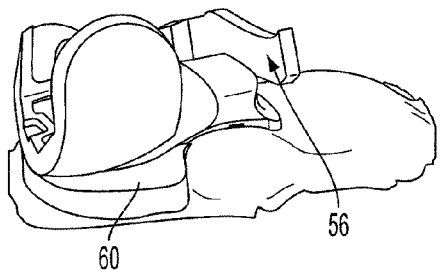
FIG. 16 is a side perspective view of the medial knee prosthesis of FIG. 15.

Although in the illustrated embodiment of FIGS. 2, 13, and 14 the femoral notch structure 32 is integrally formed with the femoral implant 26, in some embodiments, the femoral notch structure and the femoral implant can be discrete elements. FIGS. 15 and 16 illustrate an exemplary embodiment of a prosthesis including a discrete femoral notch structure 56 and a discrete femoral implant 58. Such a discrete femoral notch structure 56 can be independently mounted on the femoral bone. A tibial implant 60 in the embodiment of FIGS. 15 and 16 can articulate against the femoral implant 58, and an ACL-substituting tibial post 62 coupled to a tibia bone 64 can articulate against the femoral notch structure 56 that is independently mounted on the femoral bone.

Figure 17:
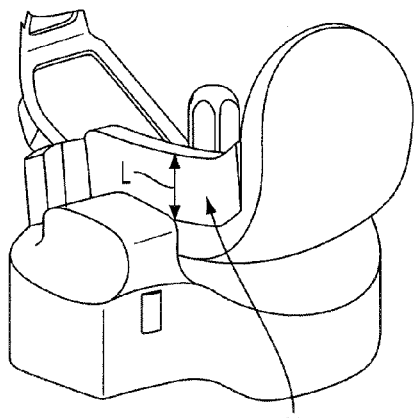
FIG. 17 is a perspective view of one embodiment of a lateral knee prosthesis in an extended or closed position.
Figure 18:
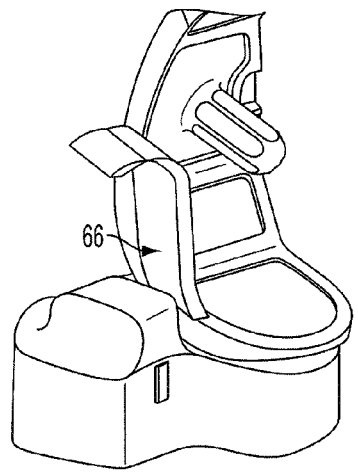
FIG. 18 is a perspective view of the prosthesis of FIG. 17 in a flexed or open position.
Figure 19:
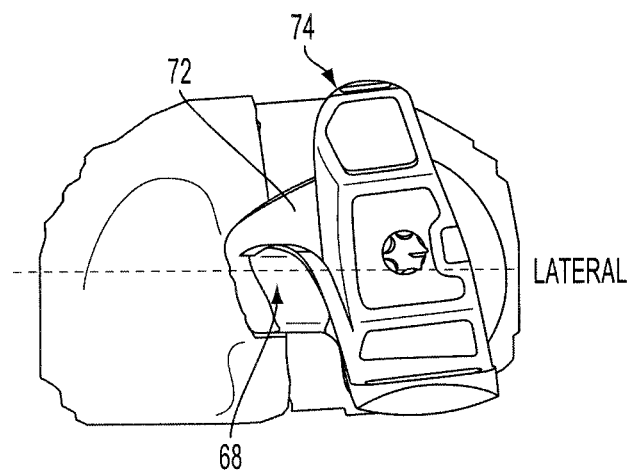
FIG. 19 is a top view of one embodiment of a lateral knee prosthesis attached to a tibia, the prosthesis including a post having a rounded top.
Figure 20A:
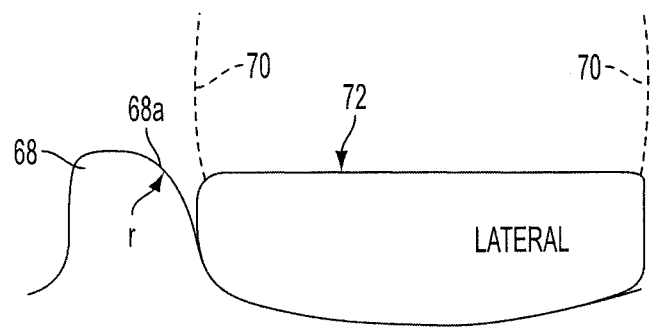
FIG. 20A is a side schematic view of the prosthesis of FIG. 19.
Figure 20B:
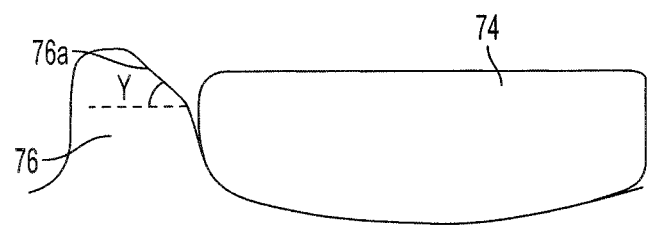
FIG. 20B is a side schematic view of one embodiment of a lateral knee prosthesis attached to a tibia, the prosthesis including a post having an angled or chamfered top.

In addition to articulating against a tibial post, a femoral notch structure can be configured to prevent the post from impinging on the lateral femoral bone through the full range of knee flexion, e.g., between extended and flexed positions of the knee. In an exemplary embodiment, a height of the femoral notch structure can be configured to prevent such impingement, such as by being in a range of about 1 to 30 mm, e.g., in a range of about 2 to 15 mm, in a range of about 1 to 20 mm, in a range of about 5 to 15 mm, about 10 mm, etc. FIGS. 17 and 18 illustrate an exemplary embodiment of a lateral prosthesis in which a height L of a femoral notch structure 66 of a prosthesis is configured to prevent a tibial post from impinging on the lateral femoral bone between an extended position (FIG. 18) and a flexed position (FIG. 17). The notch structure's height L can be in a range of about 1 to 30 mm, e.g., in a range of about 5 to 15 mm, in a range of about 1 to 20 mm, about 10 mm, etc. In the embodiment shown in FIGS. 17 and 18, the notch structure 66 is separate from the femoral implant such that it is configured to be independently mounted to a femoral bone, but as mentioned above, a notch structure can be integrally formed with a femoral implant. Alternatively or in addition to a height of a femoral notch structure, an edge of a tibial post can be configured to prevent the post from impinging on the lateral femoral bone through the full range of knee flexion. As in an exemplary embodiment illustrated in FIGS. 19 and 20A, a lateral edge of an ACL-substituting tibial post 68 of a tibial insert of a lateral prosthesis can be rounded at a tip 68a thereof at a radius r, and a height of the post 68 can be configured to avoid impingement with lateral femoral bone 70. Being rounded at the tip 68a can allow the tibial post 68 to avoid impingement with the lateral femoral bone 70. The radius r can be, e.g., in a range of about 2 to 25 mm. FIGS. 19 and 20A also show the tibial insert coupled to a femoral component 72. FIG. 20B illustrates another embodiment of a lateral edge of an ACL-substituting tibial post 76 of a tibial insert of a lateral prosthesis that can be chamfered or cut at an angle γ. At a tip 76a thereof.

The angle γ can be in a range of about 5 to 70°. Being chamfered or angled at the tip 76a can allow the tibial post 76 to avoid impingement with the lateral femoral bone. FIG. 20B also shows the tibial insert coupled to a femoral component 74.

Figure 20C:
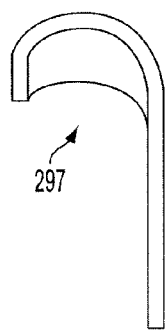
FIG. 20C is a side view of an embodiment of a bone shaping tool.
Figure 20D:
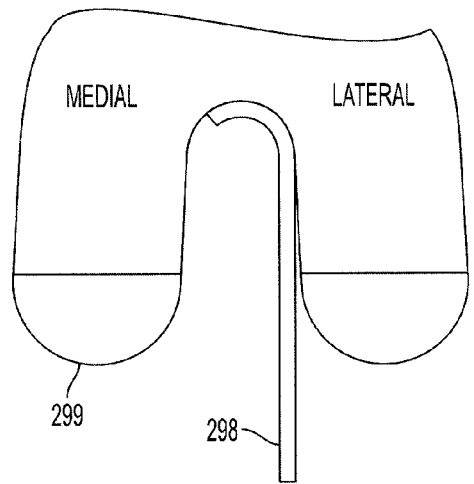
FIG. 20D is a top view of another embodiment of a bone shaping tool adjacent to an embodiment of a femoral component.

Alternatively or in addition to a height of a femoral notch structure and/or an edge of a tibial post, the lateral femoral condyle bone can be contoured during surgery to prevent the post from impinging on the lateral femoral bone, e.g., bone overhanging into the femoral notch, through the full range of knee flexion. As will be appreciated by a person skilled in the art, the lateral femoral condyle bone can be contoured in a variety of ways, such as by using a bone shaping tool, e.g. a burr, a reciprocating saw, etc. In an exemplary embodiment, the bone shaping tool has a geometry configured to match the femoral component's intercondylar notch, which can help ensure clearance of bone in the intercondylar region. FIGS. 20C and 20D illustrate embodiments of such bone shaping tools 297, 298, with the bone shaping tool 299 of FIG. 20D being shown adjacent to a femoral component 299 having an intercondylar notch with matching geometry to the tool 299.

Figure 20E:
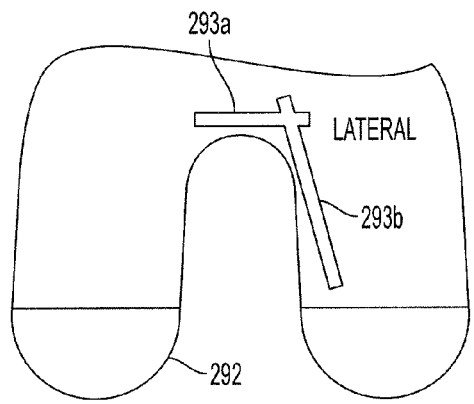
FIG. 20E is a top view of an embodiment of a femoral trial component that includes one or more guiding slots.
Figure 20F:
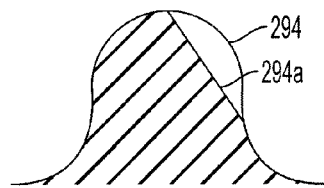
FIG. 20F is a side view of an embodiment of a trial tibial insert that has a larger size than an embodiment of a tibial insert.
Figure 20G:
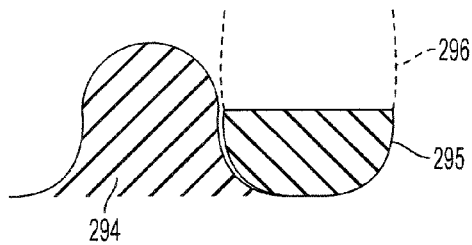
FIG. 20G is a side view of the trial tibial insert of FIG. 20F positioned adjacent a femoral bone and an embodiment of a femoral component.

A prosthesis can include one or more guiding slots configured to facilitate the bone contouring, e.g., by providing adequate clearance for tool(s) used to contour the bone and/or by providing adequate bony under hang (e.g., under hang in a range of about 1 to 5 mm). The one or more guiding slots can be formed in a femoral component of a prosthesis or in a femoral trial component inserted into a patient prior to implantation of a femoral component and, in an exemplary embodiment, can include at least one guiding slot in a lateral portion of the femoral component. FIG. 20E illustrates an embodiment of a femoral trial component 292 including two guiding slots 293a, 293b in a lateral portion of the femoral trial component 292, although any number of slots can be provided. If multiple guiding slots are provided, the guiding slots 293a, 293b can intersect one another, which can allow a tool to smoothly transition between slots oriented at different angles in the femoral trial component 292. In some embodiments, a trial tibial insert can include a tibial post having a larger size than a tibial post coupled to a tibial insert to be implanted after the "trial" insertion of the trial tibial insert, which can help ensure that enough bone has been cleared so as to not impinge bone against the tibial post coupled to the tibial insert to be implanted. FIGS. 20F and 20G illustrate an embodiment of a trial tibial post 294 of a tibial insert that has a larger size than a tibial post 294a of a tibial insert to be implanted. FIG. 20G shows the trial tibial post 294 adjacent a femoral component 295 and a femoral bone 296.

The femoral intercondylar notch can have a profile substantially matching that of a tibial post. Substantially matching the profiles of the femoral intercondylar notch and the post can allow the post to guide femoral rotation and can maintain continuous contact with the femoral notch even if the femoral component is rotationally mal-aligned with respect to the tibia. As discussed above, the medial edge of an ACL substituting post can be contoured to avoid impingement with the PCL and can have a generally curved or straight profile. As in an exemplary embodiment illustrated in FIG. 21, a tibial post 78 of a lateral prosthesis and a lateral femoral intercondylar edge 80 can have substantially matching concentric circular profiles. In an exemplary embodiment, a radius r5 of the circular profiles can be in a range of about 3 to 50 mm, e.g., in a range of about 5 to 30 mm, in a range of about 8 to 15 mm, about 10 mm, etc. In another exemplary embodiment illustrated in FIGS. 21A, 21B, 21C, and 21D, a contour of a medial edge 77a and a posterior edge 77b of a tibial post 77 can be configured to prevent impingement of a PCL in the form of angled cuts. In an exemplary embodiment, an angle θ of the posterior edge 77b can be in a range of about 3° to 80°, and an angle ψ of the medial edge 77a can be in a range of about 3° to 80°.

Figure 22:
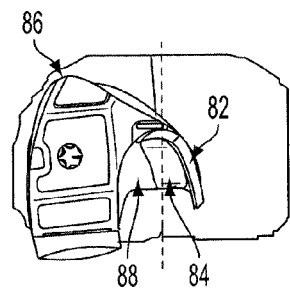
FIG. 22 is a top view of one embodiment of a medial knee prosthesis attached to a tibia, the prosthesis having a convex tibial post and a convex femoral intercondylar notch.
Figure 23:
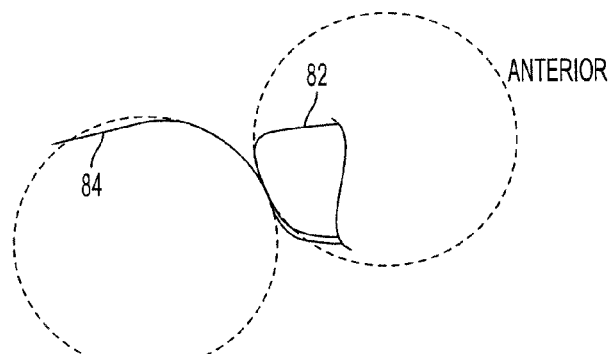
FIG. 23 is a schematic, sagittal plane cross-sectional view of the prosthesis of FIG. 22.
Figure 24:
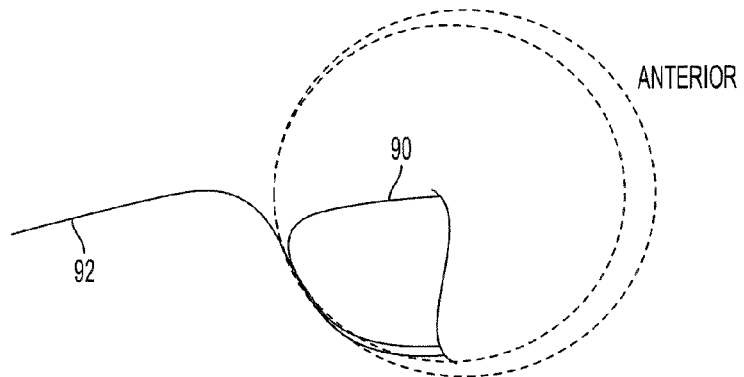
FIG. 24 is a schematic, sagittal plane cross-sectional view of one embodiment of a medial knee prosthesis, the prosthesis having a concave tibial post and a convex femoral intercondylar notch.
Figure 25:
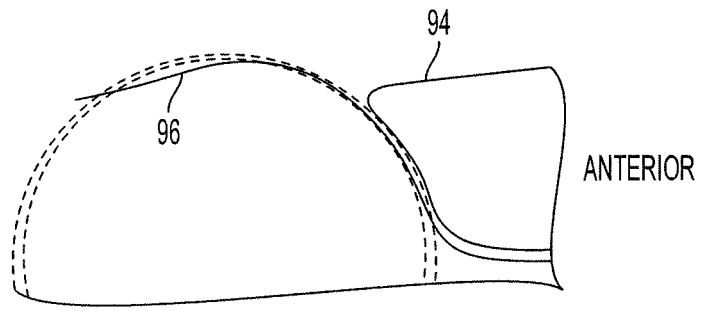
FIG. 25 is a schematic, sagittal plane cross-sectional view of one embodiment of a medial knee prosthesis, the prosthesis having a convex tibial post and a concave femoral intercondylar notch.
Figure 26:
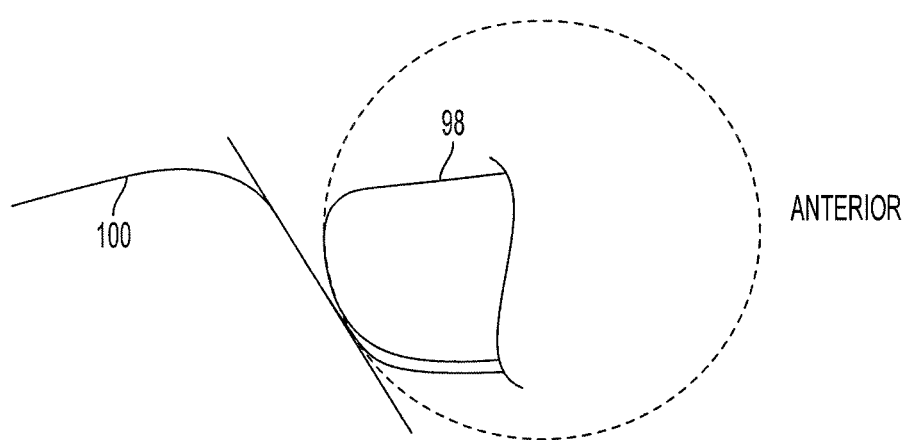
FIG. 26 is a schematic, sagittal plane cross-sectional view of one embodiment of a medial knee prosthesis, the prosthesis having a flat tibial post and a convex femoral intercondylar notch.
Figure 27:
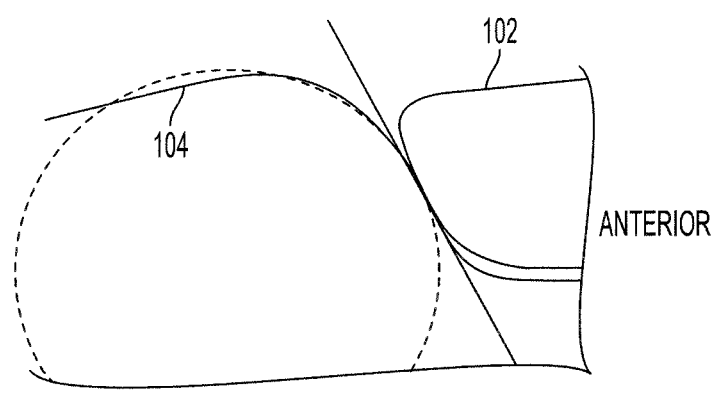
FIG. 27 is a schematic, sagittal plane cross-sectional view of one embodiment of a medial knee prosthesis, the prosthesis having a convex tibial post and a flat femoral intercondylar notch.

FIGS. 22-27 illustrate various embodiments of prostheses having posts and femoral intercondylar notches with substantially matching profiles. Generally, in these embodiments, an anterior edge of a tibial post has a convex, concave, or flat profile and can engage with an anterior edge of a femoral notch, which also has a convex, concave or flat profile. In an exemplary embodiment, a radius of the convex profile or the concave profile can be in a range of about 3 to 50 mm, e.g., in a range of about 5 to 30 mm, in a range of about 8 to 15 mm, about 10 mm, etc. FIGS. 22 and 23 illustrate a convex femoral notch 82 of a femoral component 86 engaging with a tibial insert 88 with a tibial post 84 having a convex profile. FIG. 24 illustrates an embodiment of a convex femoral notch 90 engaging with a tibial post 92 having a concave profile. FIG. 25 illustrates an embodiment of a concave femoral notch 94 engaging with a tibial post 96 having a convex profile. FIG. 26 illustrates an embodiment of a convex femoral notch 98 engaging with a tibial post 100 having a flat profile. FIG. 27 illustrates an embodiment of a flat femoral notch 102 engaging with a tibial post 104 having a convex profile.

Figure 28:
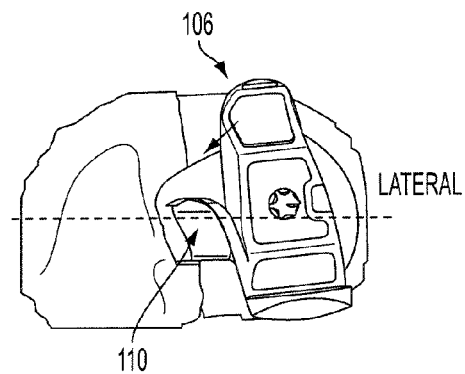
FIG. 28 is a top view of one embodiment of a lateral knee prosthesis attached to a tibia, the prosthesis having a concave tibial post and a convex femoral intercondylar notch.
Figure 29:
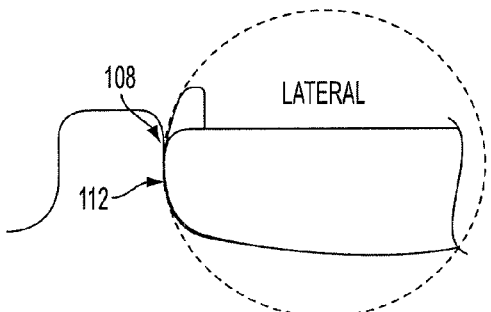
FIG. 29 is a schematic, coronal plane cross-sectional view of the prosthesis of FIG. 28.
Figure 30:
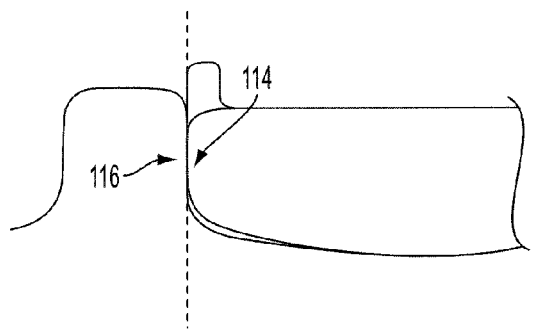
FIG. 30 is a schematic, coronal plane cross-sectional view of one embodiment of a lateral knee prosthesis attached to a tibia, the prosthesis having a flat tibial post and a flat femoral intercondylar notch.
Figure 31:
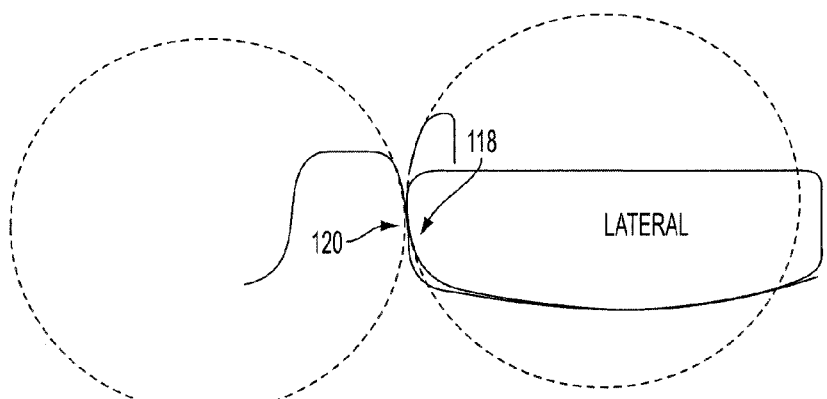
FIG. 31 is a schematic, coronal plane cross-sectional view of one embodiment of a lateral knee prosthesis attached to a tibia, the prosthesis having a convex tibial post and a convex femoral intercondylar notch.
Figure 32:
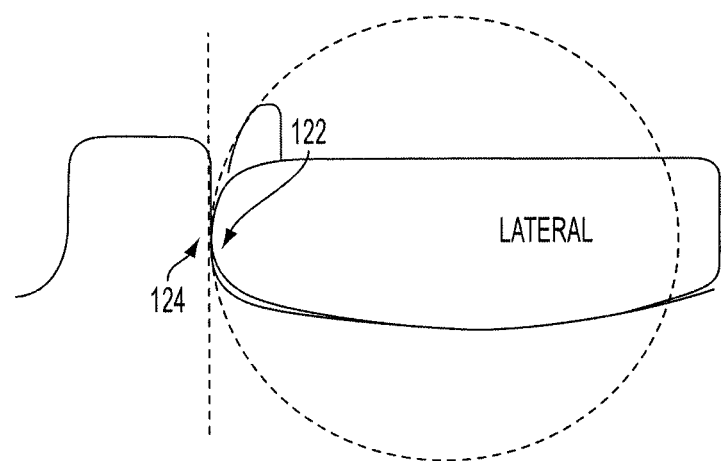
FIG. 32 is a schematic, coronal plane cross-sectional view of one embodiment of a lateral knee prosthesis attached to a tibia, the prosthesis having a flat tibial post and a convex femoral intercondylar notch.
Figure 33:
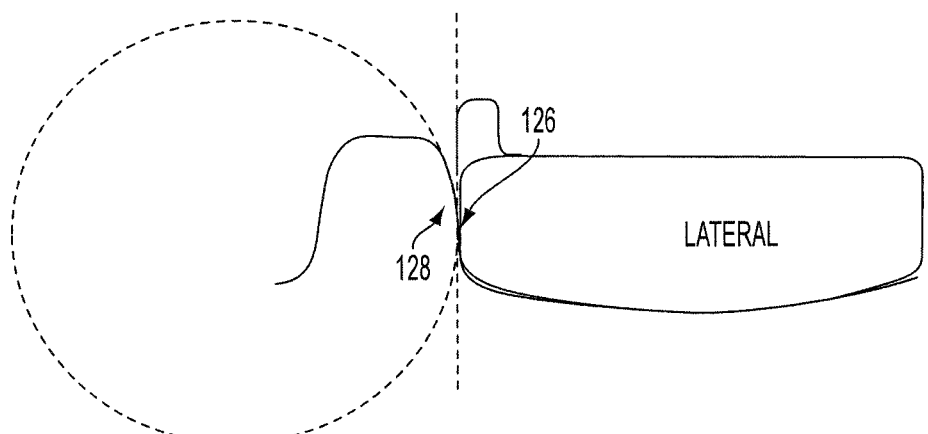
FIG. 33 is a schematic, coronal plane cross-sectional view of one embodiment of a lateral knee prosthesis attached to a tibia, the prosthesis having a convex tibial post and a flat femoral intercondylar notch.

FIGS. 28-33 illustrate various embodiments of prostheses having posts and femoral intercondylar notches with substantially matching profiles. Generally, in these embodiments, a tibial post occupies a lateral portion of the intercondylar region, and both a lateral edge of a tibial post and a mating femoral notch can have a convex, concave, or flat profile. In an exemplary embodiment, a radius of the convex profile or the concave profile can be in a range of about 3 to 50 mm, e.g., in a range of about 5 to 30 mm, in a range of about 8 to 15 mm, about 10 mm, etc. FIGS. 28 and 29 illustrate an embodiment of a convex femoral notch 108 of a femoral component 106 engaging with a tibial insert 110 with a tibial post 112 having a concave profile. FIG. 30 illustrates an embodiment of a flat femoral notch 114 engaging with a tibial post 116 having a flat profile. FIG. 31 illustrates an embodiment of a convex femoral notch 118 engaging with a tibial post 120 having a convex profile. FIG. 32 illustrates an embodiment of a convex femoral notch 122 engaging with a tibial post 124 having a flat profile. FIG. 33 illustrates an embodiment of a flat femoral notch 126 engaging with a tibial post 128 having a convex profile.

Figure 68:
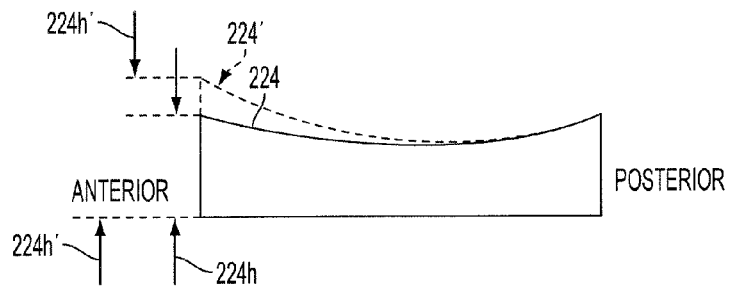
FIG. 68 is a medial/lateral cross-sectional view of one embodiment of a tibial insert of a knee prosthesis having a reduced articular surface.
Figure 69A:
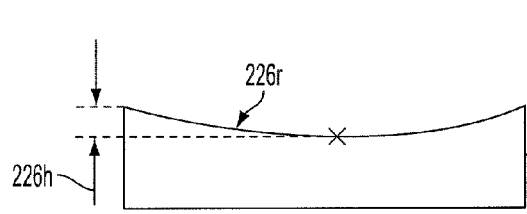
FIG. 69A is a medial/lateral cross-sectional view of another embodiment of a tibial insert of a knee prosthesis having a reduced articular surface.
Figure 69B:
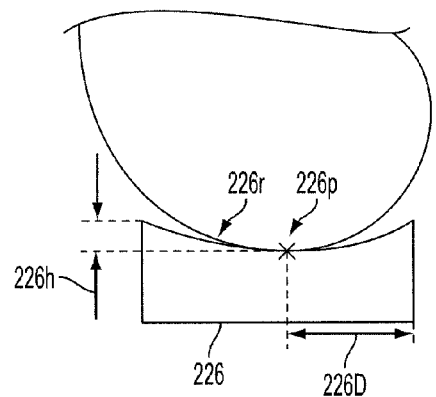
FIG. 69B is a side view of the tibial insert of FIG. 69A adjacent a femur.
Figure 70:
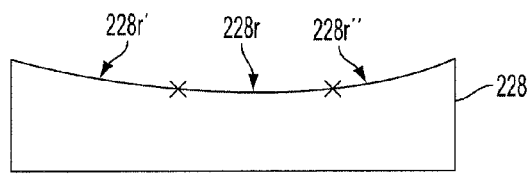
FIG. 70 is a medial/lateral cross-sectional view of yet another embodiment of a tibial insert of a knee prosthesis having a reduced articular surface.

As mentioned above, embodiments of prostheses described herein can be configured to substitute function of an ACL at least during early knee flexion, such as by a tibial insert of the prosthesis including a tibial post configured to eliminate abnormal posterior subluxation of the femur in early knee flexion. Conventional tibial insert articular surfaces can, however, have a relatively high anterior lip height, e.g., in a range from about 6 to 11 mm, which may hinder effectiveness of the tibial post in substituting ACL function. Thus, tibial insert articular surfaces of prostheses described herein can have a lower anterior lip height, e.g., in a range of about 0 to 6 mm, e.g., less than 6 mm, than an anterior lip height in conventional tibial inserts. FIG. 68 illustrates an embodiment of a tibial insert 224 having an anterior lip height 224h that is less than an anterior lip height 224h' of a conventional tibial insert 224', shown by dotted line in FIG. 68. FIGS. 69A and 69B illustrate an embodiment of a tibial insert 226 having an anterior radius 226r, e.g., in a range of about 70 to 150 mm, that is higher than an anterior radius, e.g., in a range of about 30 to 60 mm, of a conventional tibial insert, thereby allowing an anterior lip height 226h of the tibial insert 226 to be lower than an anterior lip height of the convention tibial insert. The anterior radius 226r of the tibial insert 226 can be two or more times larger, e.g., over four times larger, than that of a conventional tibial insert. To allow for the lower anterior lip height 226h, a low point 226p of the tibial insert 226 can be located more anteriorly than a low point of a conventional tibial insert such that a distance 226D between the low point 226p and a lateral edge of the tibial insert 226 can be greater than a distance between a low point and a lateral edge of the conventional tibial insert. FIG. 70 illustrates an embodiment of a tibial insert 228 having a lower anterior lip height than a conventional tibial insert by having an intermediate radius 228r, located between an anterior radius 228r' and a posterior radius 228r'' of the tibial insert 228, that can be substantially larger than the anterior radius 228r'. The intermediate radius 228 can be, e.g., in a range of about 70 to 300 mm, and the anterior radius 228r' can be, e.g., in a range of about 30 to 60 mm. The intermediate radius 228 of the tibial insert 228 can therefore be two or more times larger, e.g., at about five times larger, than that of a conventional tibial insert. In some embodiments, the intermediate radius 228r can be substantially flat.

Figure 71:
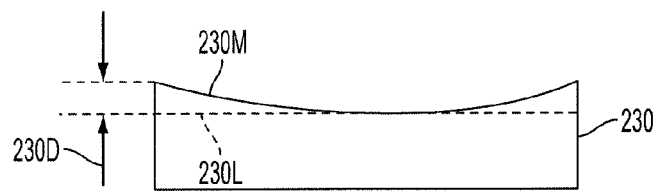
FIG. 71 is a medial/lateral cross-sectional view of an embodiment of a tibial insert having a concave medial profile and a convex lateral profile.

Medial and lateral anterior lip heights of a tibial insert can have different heights to allow for ACL substitution at least during early knee flexion. In a normal knee, the ACL attaches to the lateral femoral condyle and pulls the ACL more anteriorly on the tibia than the medial femoral condyle. Thus, generally, an anterior medial lip height of a tibial insert can be greater than an anterior lateral lip height of the tibial insert. Medial and lateral tibial insert profiles can be different from one another to reflect this normal ACL function. FIG. 71 illustrates an embodiment of a tibial insert 230 having a convex lateral profile 230L and a concave medial profile 230M. These profile geometries can result in an anterior medial lip height that is greater than an anterior lateral lip height by an amount 230D, e.g., greater by at least 1 mm, e.g., in a range of about 1 to 10 mm. These profile geometries can allow the lateral femoral condyle to be located more anteriorly than the medial femoral condyle.

Figure 72:
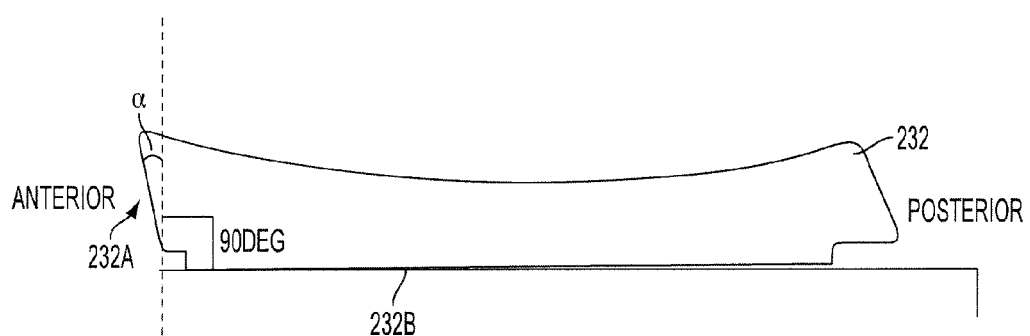
FIG. 72 is a medial/lateral cross-sectional view of an embodiment of a tibial insert having an angled anterior edge.

In some embodiments, an anterior edge of a tibial insert can extend at an angle relative to a base of the tibial insert, which can allow for ACL substitution at least during early knee flexion by increasing a tibiofemroal contact area during knee extension. The anterior location of a femoral component on a tibia due to engagement of the femoral component against the tibial insert's post can pull the femur forward on the tibia. Thus, in extension and particularly in hyperextenstion, the femoral component contacts the tibial insert at its anterior edge. The angled anterior edge can therefore increase tibiofemoral contact. FIG. 72 illustrates an embodiment of a tibial insert 232 having an anterior edge 232A extending at a non-zero angle α relative to a base 232B of the tibial insert 232 such that the anterior edge 232A extends anteriorly at the non-zero angle α. The angle α can be up to about 30°, e.g., about 15°, up to about 5°, in a range of about 5° to 10°, in a range of about 10° to 20°, in a range of about 20° to 30°, etc.

Figure 73:
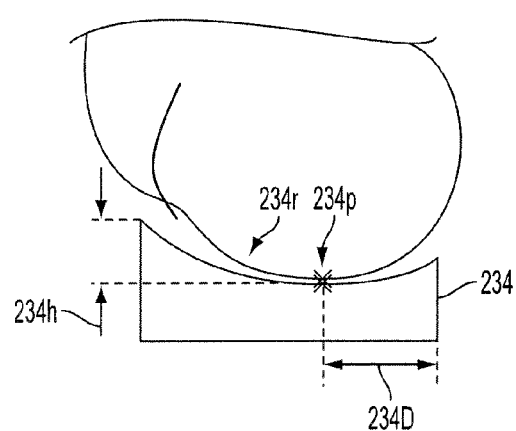
FIG. 73 is a medial/lateral cross-sectional view of an embodiment of a tibial insert of a knee prosthesis having a reduced distal femoral condyle radius, the tibial insert shown adjacent a femur.

Instead of reducing an anterior lip height of a tibial insert as compared to a conventional tibial insert, a distal femoral condyle radius of a femoral implant can be reduced as compared to a conventional tibial insert, thereby allowing a prosthesis including the femoral implant to substitute function of an ACL at least during early knee flexion. FIG. 73 illustrates an embodiment of a tibial insert 234 having a reduced distal femoral condyle radius 234r. The distal femoral condyle radius 234r is medial in the illustrated example, but similar to that mentioned above regarding medial/lateral prostheses, a distal femoral condyle radius of a tibial insert can be lateral, thereby allowing an anterior lip height 234h of the tibial insert 234 to be greater than or equal to an anterior lip height of the convention tibial insert, and still allow for ACL substitution function without impediment. To allow for the greater anterior lip height 234h, a low point 234p of the tibial insert 234 can be located more posterior than a low point of a conventional tibial insert such that a distance 234D between the low point 234p and a lateral edge of the tibial insert 234 can be greater than a distance between a low point and a lateral edge of the conventional tibial insert.

As mentioned above, prostheses described herein can be configured for use in total knee replacement surgical procedures. Generally, total knee replacement prostheses can be configured similarly to the partial knee replacement prostheses discussed above and variously illustrated in FIGS. 2-33 and 68-73 except that the total knee replacement prostheses can be configured to resurface both a medial tibial compartment and a lateral tibial compartment. In other words, a total knee replacement prosthesis can be configured to be seated on the medial and lateral tibial compartment to provide total knee replacement and an ACL substitution. Like-named elements of partial knee replacement prostheses and total knee replacement prostheses discussed herein can generally be similarly configured.

Figure 34:
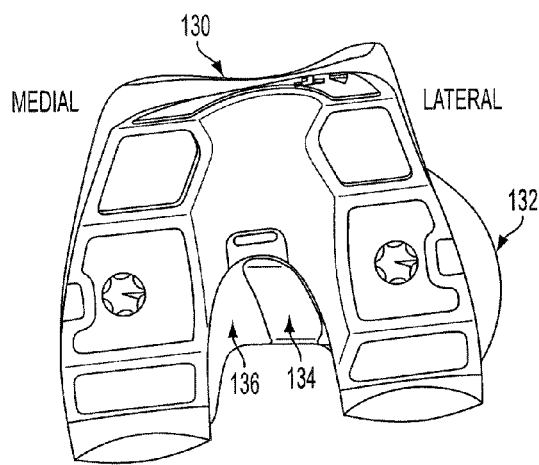
FIG. 34 is a top perspective view of one embodiment of a total knee replacement prosthesis.
Figure 35:
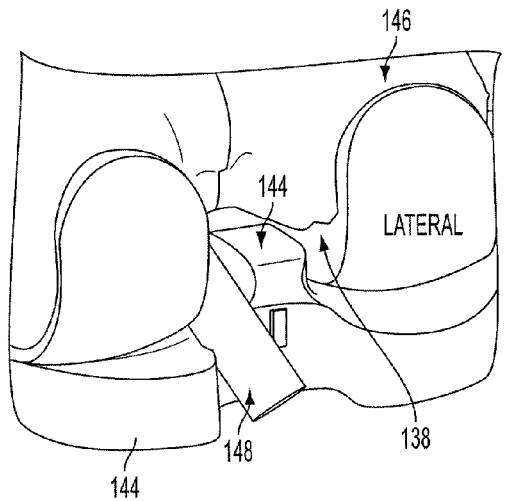
FIG. 35 is a perspective view of one embodiment of a total knee replacement prosthesis attached to a femur, the prosthesis being in an extended or closed position and including a femoral notch structure.
Figure 36:
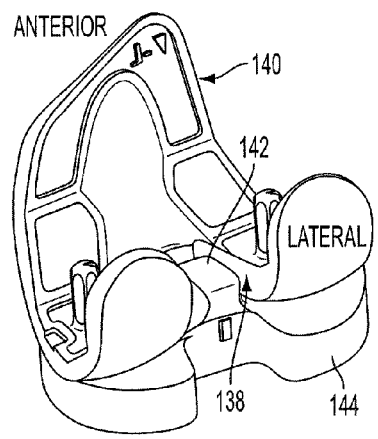
FIG. 36 is a perspective view of the prosthesis of FIG. 35 not attached to bone and in a flexed or open position.

FIG. 34 illustrates an exemplary embodiment of a knee replacement prosthesis configured to provide substitution of an ACL in total knee replacement surgery. As in the illustrated embodiment, the prosthesis can include a femoral implant 130, a tibial implant 132, and an ACL-substituting post 134. The tibial implant 132 can include a space 136 adjacent the post 134 configured to accommodate a PCL (not shown). A prosthesis configured for total knee replacement surgery can also include a femoral component 140 including a femoral notch structure 138, such as in an exemplary embodiment illustrated in FIGS. 35 and 36. FIGS. 35 and 36 show the femoral component 140 coupled to a tibial insert 142 including a tibial post 144, and FIG. 35 shows a posterior view of the femoral component 140 coupled to a femoral bone 146 and the prosthesis seating a PCL 148, which is illustrated as a cylinder.

Figure 37:
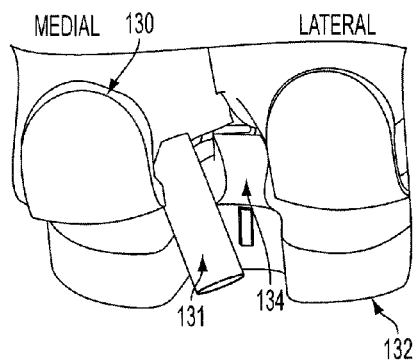
FIG. 37 is a perspective view of the prosthesis of FIG. 34 attached to a femur and showing a representation of a PCL ligament.
Figure 38:
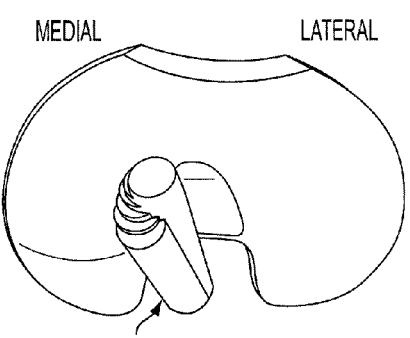
FIG. 38 is a perspective view of the prosthesis of FIG. 37 not attached to bone and with the representation of the PCL ligament in positions corresponding to different knee flexion angles.
Figure 39:
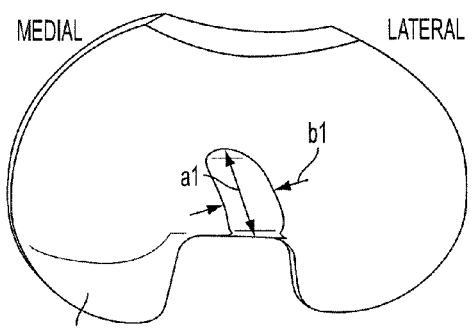
FIG. 39 is a top view of a tibial implant of the prosthesis of FIG. 34.
Figure 40:
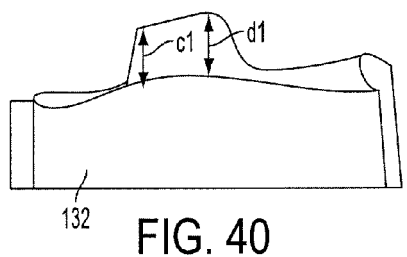
FIG. 40 is a side view of the tibial implant of FIG. 39.
Figure 41:
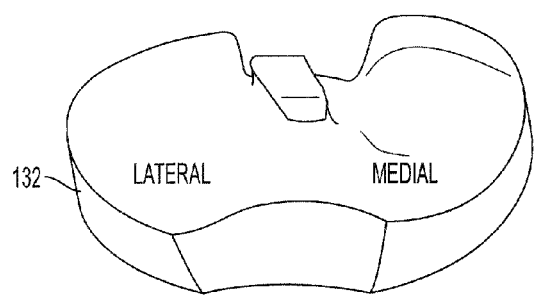
FIG. 41 is a perspective view of the tibial implant of FIG. 39.

FIG. 37 illustrates a posterior view of the prosthesis of FIG. 34 in use with the patient's PCL ligament 131 being represented as a cylinder joining the tibial insertion of the ligament 131 to its insertion on the medial femoral condyle within the intercondylar region. FIG. 38 shows the prosthesis and PCL ligament 131 of FIG. 37 with the PCL ligament 131 in different positions corresponding to different knee flexion angles between about 0° to 70°. FIGS. 39-43 illustrate the tibial implant 132 of the prosthesis of FIG. 34 and variously include reference characters a1, b1, c1, d1, e1, f1, g1, and h1 respectively corresponding to length, width, posterior height, anterior height, and distances of the post 134 similar to that discussed above with reference to FIGS. 6-10. As shown, for example, in FIGS. 42 and 43, the tibial implant 132 in a total knee replacement prosthesis can be generally kidney-shaped to substantially match the tibial surfaces to which it can be affixed.

Figure 45:
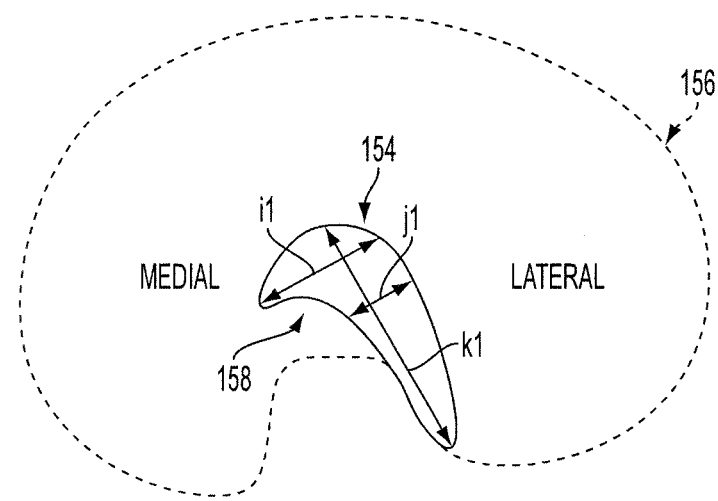
FIG. 45 is a schematic view of one embodiment of a total knee replacement prosthesis including a tibial post and a tibial insert, the tibial post having a lateral edge extending back to a posterior edge of the tibial insert.

FIGS. 44 and 45 illustrate exemplary embodiments of total knee replacement prostheses that are respectively similar to the embodiments of FIGS. 11 and 12 discussed above. FIG. 44 illustrates an exemplary embodiment of a prosthesis including a gradually blending tibial post 150 adjacent a space 152 for a PCL. FIG. 45 illustrates an exemplary embodiment of a prosthesis including a tibial insert having an extending post 154, the post 154 having an anterior width i1, a central width j1, and a length k1. FIG. 45 shows a base profile 156 of the tibial insert by dotted outline, with a space 158 for a PCL (not shown) being located adjacent the post 154.

Figure 46:
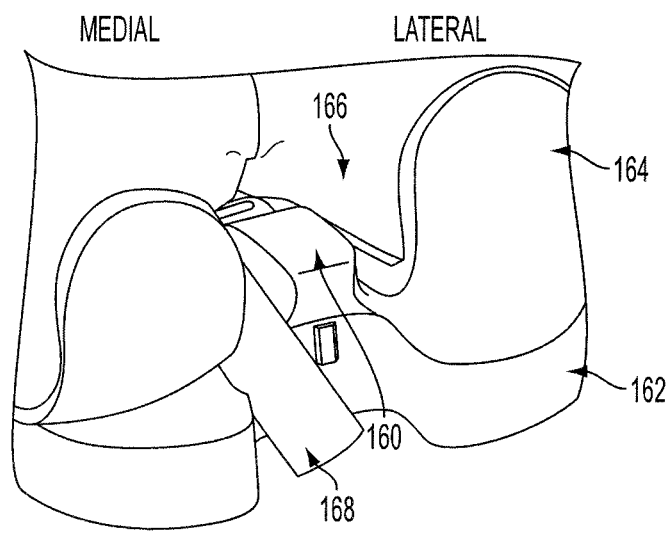
FIG. 46 is a perspective view of one embodiment of a total knee replacement prosthesis attached to a femur and having a post with a height configured to avoid impingement with the lateral femoral condyle.

As discussed above, a notch structure and/or a post can be configured to prevent the post from impinging on the lateral femoral bone through the full range of knee flexion. FIG. 46 illustrates an exemplary embodiment of a prosthesis having a tibial insert 162 having a post 160 with a height configured to avoid impingement with the lateral femoral condyle. The prosthesis can also include a femoral component 164 adjacent a femoral bone 166. The patient's PCL ligament 168 is represented as a cylinder. FIGS. 47 and 48, similar to FIGS. 19 and 20A, illustrate an exemplary embodiment of a prosthesis having a lateral edge of an ACL-substituting tibial post 170 of a lateral prosthesis rounded on top. FIGS. 47 and 48 also illustrate a femoral component 172 mated to a tibial insert 174 that includes the post 170. FIGS. 49 and 50, similar to FIGS. 17 and 18, illustrate an exemplary embodiment of a prosthesis in which a height L1 of the prosthesis's notch structure 176 can be configured to prevent a post 178 of a tibial implant 180 from impinging on the lateral femoral bone between an extended position (FIG. 49) and a flexed position (FIG. 50). The height L1 of the notch structure 176 can be in a range of about 1 to 20 mm, in a range of about 5 to 15 mm, about 10 mm, etc.

Figure 21:
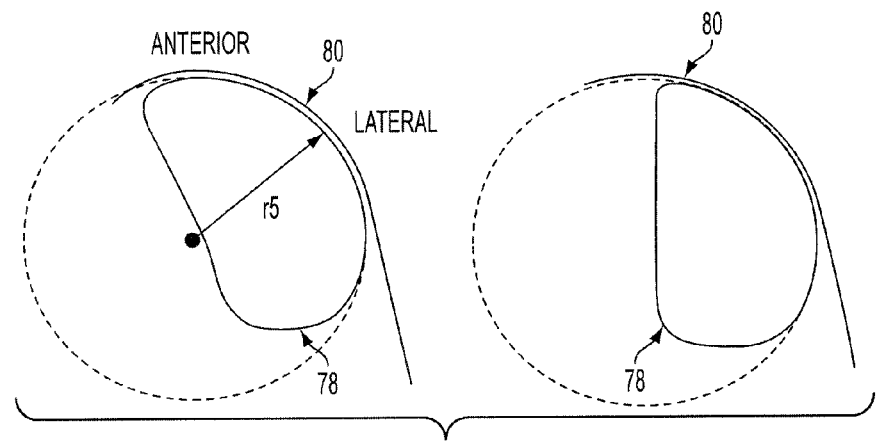
FIG. 21 are top schematic views of one embodiment of a lateral knee prosthesis including a tibial post and a femoral intercondylar structure, the post, an anterior surface, and a lateral surface of the femoral intercondylar structure having concentric circular profiles.
Figure 21A:
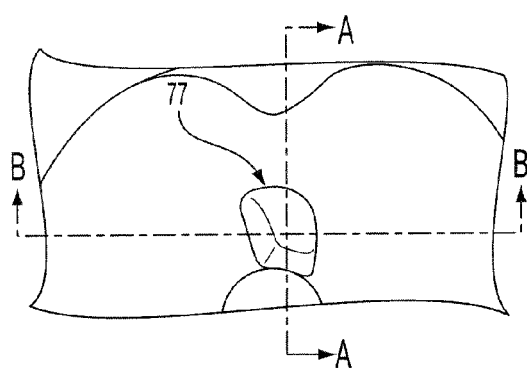
FIG. 21A is top, partial view of one embodiment of a prosthesis including a tibial post including angled cuts.
Figure 21B:
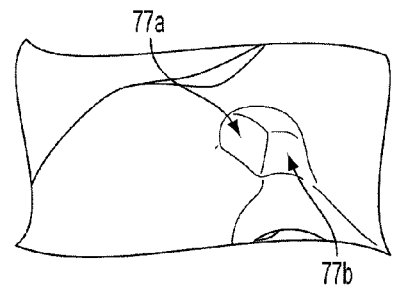
FIG. 21B is a perspective, partial view of the prosthesis of FIG. 21A.
Figure 21C:
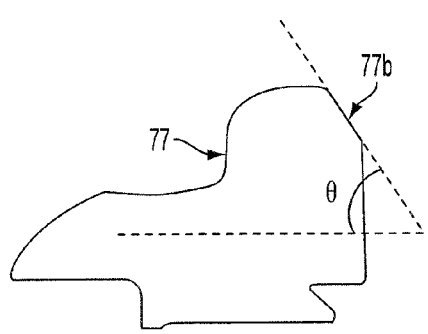
FIG. 21C is a sagittal section view A-A of the tibial insert of FIG. 21A.
Figure 21D:
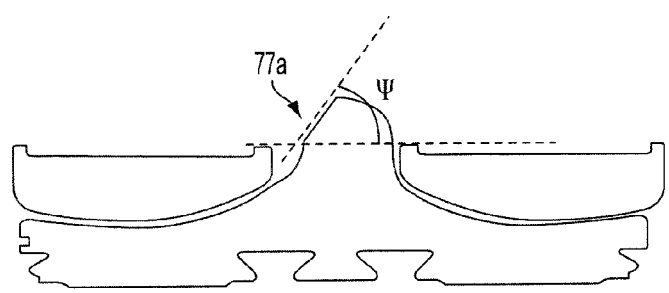
FIG. 21D is a coronal section view B-B of the tibial insert of FIG. 21A.
Figure 51:
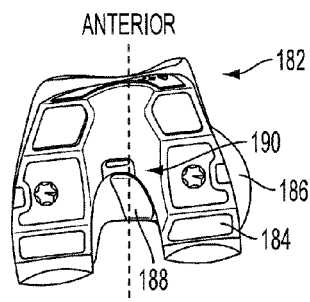
FIG. 51 is a top view of one embodiment of a total knee replacement prosthesis having a convex tibial post and a convex femoral intercondylar notch.
Figure 52:
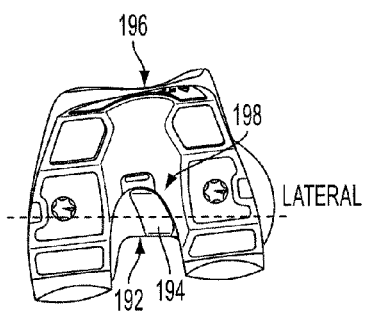
FIG. 52 is a top view of one embodiment of a total knee replacement prosthesis having a concave tibial post and a convex femoral intercondylar notch.
Figure 53:
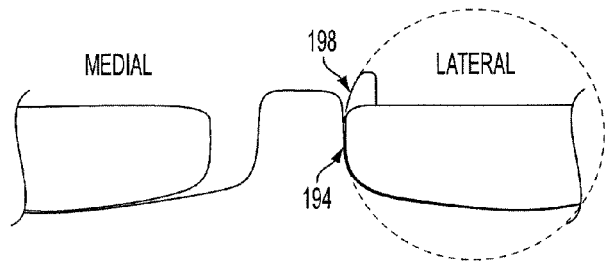
FIG. 53 is a schematic, coronal plane cross-sectional view of the prosthesis of FIG. 52 attached to a tibia.
Figure 54:
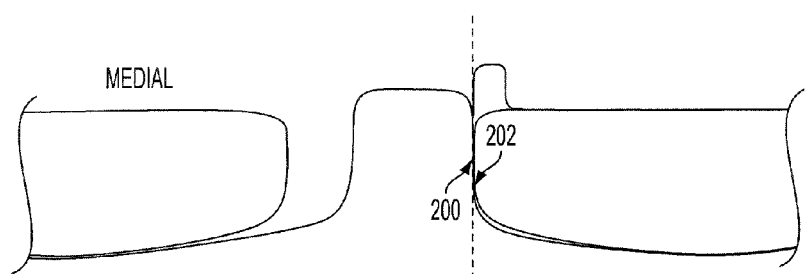
FIG. 54 is a schematic, coronal plane cross-sectional view of one embodiment of a total knee replacement prosthesis attached to a tibia, the prosthesis having a flat tibial post and a flat femoral intercondylar notch.
Figure 55:
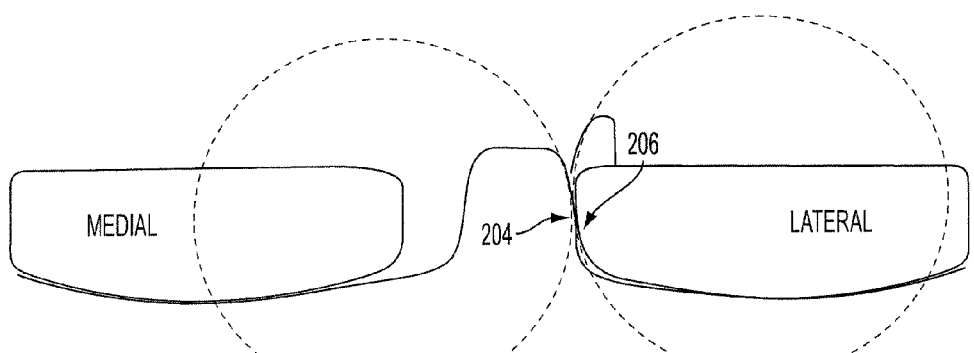
FIG. 55 is a schematic, coronal plane cross-sectional view of one embodiment of a total knee replacement prosthesis attached to a tibia, the prosthesis having a convex tibial post and a convex femoral intercondylar notch.
Figure 56:
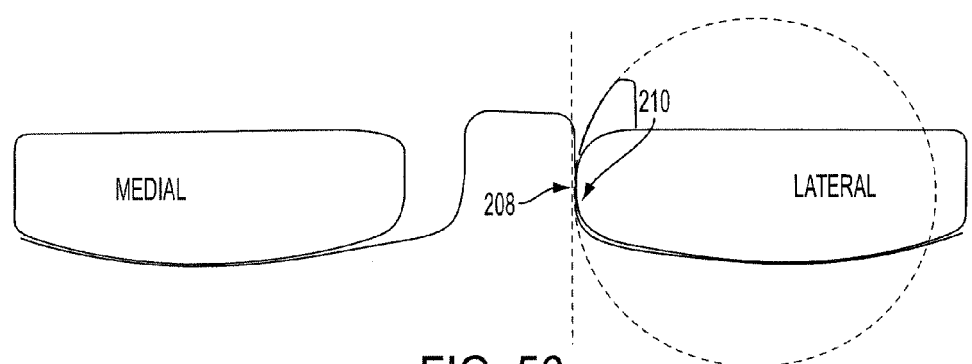
FIG. 56 is a schematic, coronal plane cross-sectional view of one embodiment of a total knee replacement prosthesis attached to a tibia, the prosthesis having a flat tibial post and a convex femoral intercondylar notch.
Figure 57:
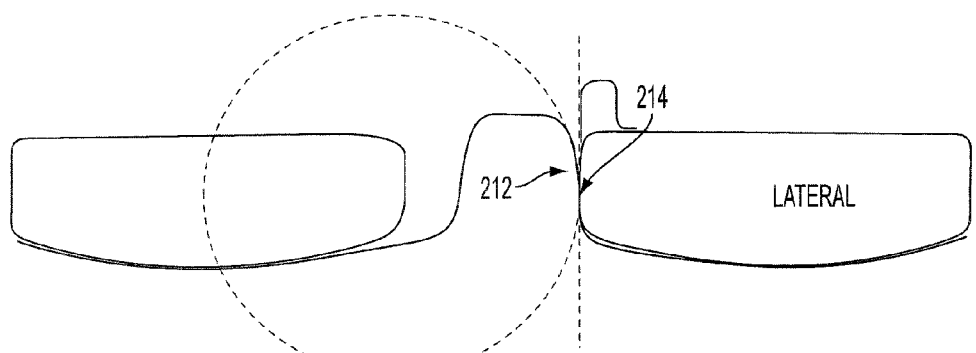
FIG. 57 is a schematic, coronal plane cross-sectional view of one embodiment of a total knee replacement prosthesis attached to a tibia, the prosthesis having a convex tibial post and a flat femoral intercondylar notch.

Similar to that discussed above, a femoral intercondylar notch of a total knee replacement prosthesis can have a profile substantially matching that of the prosthesis's post. FIG. 21 also illustrates an exemplary embodiment of a tibial post of a total knee replacement prosthesis having a concentric circular profile substantially matching concentric circular profile of anterior and lateral surfaces of the femoral intercondylar notch structure. FIGS. 23-27 discussed above also illustrate exemplary embodiments of prostheses having posts and femoral intercondylar notches with substantially matching profile, where the embodiment of FIG. 23 shows a sagittal cross section of an embodiment of a total knee replacement prosthesis 182 illustrated in FIG. 51 that includes a femoral component 184 and a tibial insert 186. The prosthesis 182 of FIG. 51 includes a convex tibial post 188 and a convex femoral intercondylar notch 190. Similar to FIGS. 28-33 discussed above, respectively, FIGS. 52-57 illustrate various embodiments of total knee replacement prostheses having posts and femoral intercondylar notches with substantially matching profiles. FIG. 52 illustrates one embodiment of a total knee replacement prosthesis having a tibial insert 192 with a concave tibial post 194 and a femoral component 196 with a convex femoral intercondylar notch 198. FIG. 53 is a coronal plane cross-sectional view of the prosthesis of FIG. 52 attached to a tibia. FIG. 54 illustrates one embodiment of a total knee replacement prosthesis attached to a tibia and having a flat tibial post 200 and a flat femoral intercondylar notch 202. FIG. 55 illustrates one embodiment of a total knee replacement prosthesis attached to a tibia and having a convex tibial post 204 and a convex femoral intercondylar notch 206. FIG. 56 illustrates one embodiment of a total knee replacement prosthesis attached to a tibia and having a flat tibial post 208 and a convex femoral intercondylar notch 210. FIG. 57 illustrates one embodiment of a total knee replacement prosthesis attached to a tibia and having a convex tibial post 212 and a flat femoral intercondylar notch 214.

In addition to a prosthesis for total knee replacement being configured for ACL substitution, the prosthesis can be configured for PCL substitution. Providing a substitute for a PCL with a knee replacement prosthesis can help reduce a number of surgical procedures needed to repair the knee and/or can help the knee's functionality approach 100% after surgery.

Figure 74A:
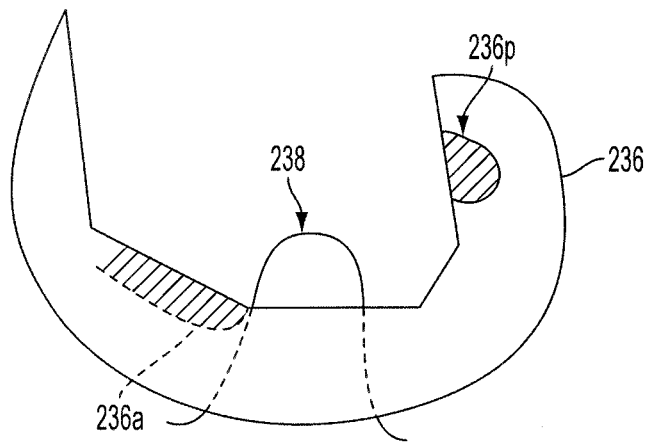
FIG. 74A is a side, partially transparent view of an ACL and PCL substituting prosthesis including a femoral component and a tibial insert including a tibial post.
Figure 74B:
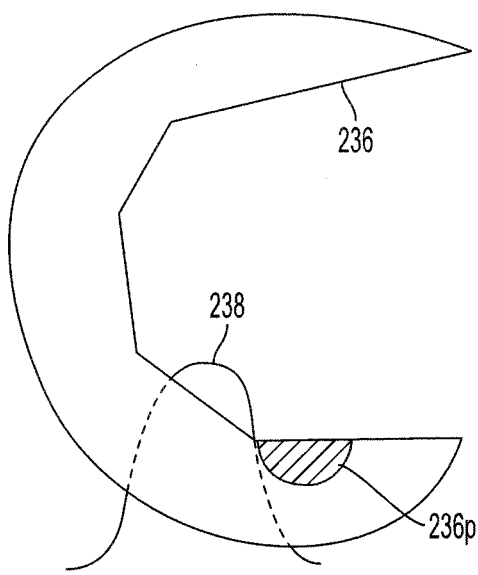
FIG. 74B is another view of the prosthesis of FIG. 74A.
Figure 75:
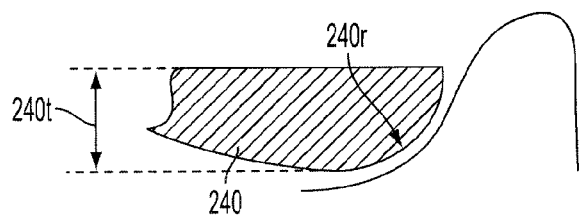
FIG. 75 is a partial side cross-sectional view of an embodiment of a femoral component mated to an anterior and posterior tibial post, the femoral component having an increased thickness and radius.
Figure 76:
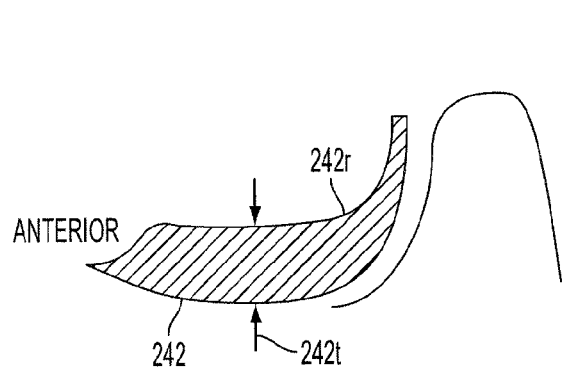
FIG. 76 is a partial side cross-sectional view of an embodiment of a femoral component mated to an anterior and posterior tibial post, the femoral component having an increased radius.

Generally, PCL and ACL substituting total knee replacement prostheses can be configured similarly to ACL-only substituting knee replacement prostheses discussed herein except that the PCL and ACL substituting total knee replacement prostheses can be configured for ACL substitution via engagement of an anterior surface of the prosthesis's tibial post with the anterior femoral intercondylar notch. In contrast, a conventional prosthesis substitutes PCL function via the engagement of a posterior femoral cam and a posterior surface of a tibial post. FIGS. 74A and 74B illustrate an embodiment of an ACL and PCL substituting total knee replacement prosthesis including a femoral component 236 including a PCL substituting cam 236p and an ACL substituting cam 236a, and a tibial insert including a tibial post 238. Because of the absence of the PCL, an intercondylar notch of the femoral component 236 can have a relatively large surface area configured to mate with the tibial post's geometry, as shown in FIGS. 74A and 74B, thereby allowing contact stresses at the mating interface to be reduced. In some embodiments, such as in an embodiment illustrated in FIG. 75, this relatively large surface area can be achieved by a thickness 240t, e.g., a thickness in a range of about 4 to 10 mm (e.g., greater than 5 mm), of a femoral notch 240 of a femoral component being greater than a thickness, e.g., in a range of about 2 to 5 mm, of a femoral notch in a conventional femoral component, and by a radius 240r, e.g., in a range of about 5 to 30 mm, of the femoral notch 240 being greater than a radius, e.g., in a range of about 2 to 5 mm, of a femoral notch in a conventional femoral component. In other embodiments, such as in an embodiment illustrated in FIG. 76A, this relatively large surface area can be achieved without increasing thickness 242t but by a radius 242r, e.g., in a range of about 5 to 30 mm, of a femoral notch 242 being greater than a radius, e.g., in a range of about 2 to 5 mm, of a femoral notch in a conventional femoral component.

Figure 77:
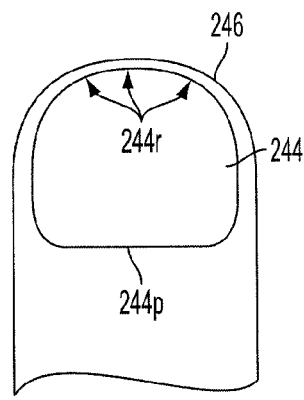
FIG. 77 is a top view of one embodiment of a tibial post having a convex profile, the tibial post engaged with a femoral notch having a rounded profile.
Figure 78:
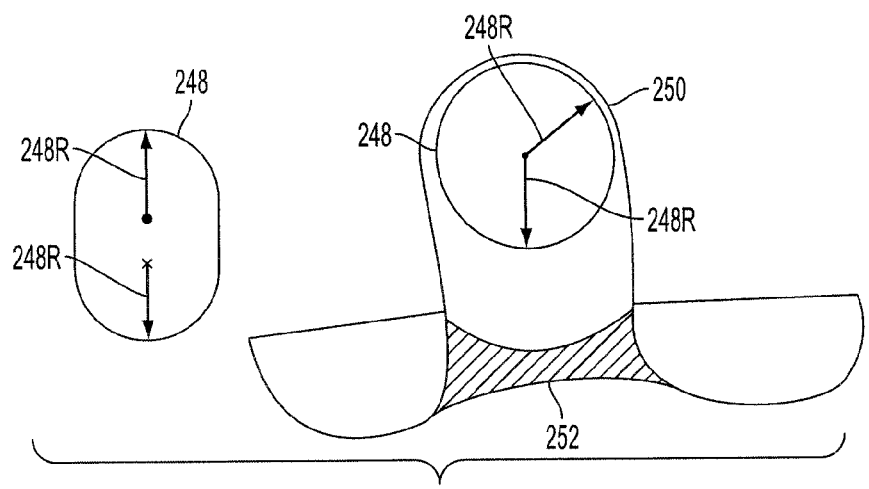
FIG. 78 is top view and a perspective view of one embodiment of a tibial post having a convex profile engaged with a femoral notch having a concave profile.
Figure 79:
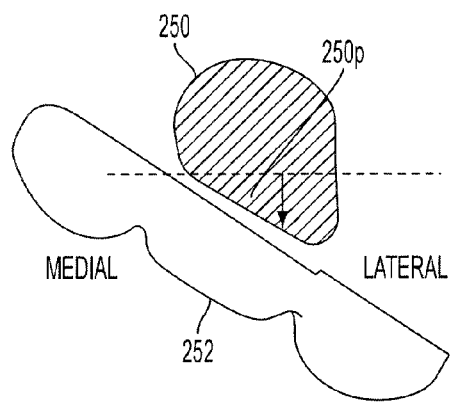
FIG. 79 is a side view of one embodiment of a tibial post engaging a femoral cam.
Figure 80A:
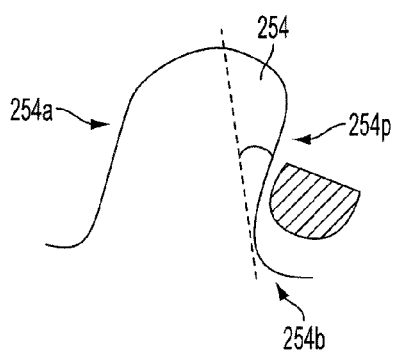
FIG. 80A is a sagittal view of an embodiment of a tibial post that is angled posteriorly.
Figure 80B:
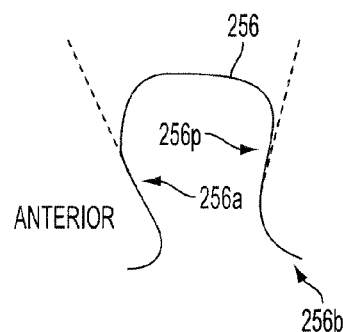
FIG. 80B is a sagittal view of an embodiment of a tibial post that has an anteriorly angled anterior surface and a posteriorly angled posterior surface.

Tibial posts of prostheses configured to substitute ACL and PCL function can have a variety of profiles. As in one embodiment shown in FIG. 77, a tibial post 244 can have a convex profile in a top-down view, which can be configured to engage a rounded geometry of a femoral notch 246 of a femoral component. The convex profile of the post 244 can have a radius 244r, e.g., in a range of about 5 to 60 mm. A posterior surface 244-p of the post 244 can have a flat profile configured to engage with a flat posterior femoral cam. In another embodiment, shown in FIG. 78, anterior and posterior surfaces of a tibial post 248 can have a convex profile configured to engage with a concave profile of a femoral intercondylar notch 250 and a posterior femoral cam 252. The convex profile of the post 248 can have a radius 248R, e.g., in a range of about 5 to 60 mm. In yet another embodiment, shown in FIG. 79, a tibial post 250 can have an angled posterior surface 250p configured to engage a posterior femoral cam 252 and configured to allow asymmetric posterior motions of the medial and lateral condyles. In a sagittal view, anterior and posterior surfaces of an ACL and PCL substituting post can be angled. The angles of the surfaces can both be anterior, both be posterior, or one of each. The angle degree of the surfaces can vary, such as being a positive angle up to about 15°. FIG. 80A illustrates one embodiment of a post 254 that is posteriorly sloped relative to a base 254b of a tibial insert including the post 254, which includes posteriorly sloped posterior and anterior surfaces 254a, 254p. FIG. 80B illustrates one embodiment of a post 256 that is anteriorly and posteriorly sloped relative to a base 256b of a tibial insert including the post 256, which includes a posteriorly sloped posterior surface 256p and an anteriorly sloped anterior surface 256a.

In any of the prosthesis embodiments disclosed herein, a tibial insert can be in a fixed, non-variable position relative to a tibial base such that a post coupled to the tibial insert, whether the post is integral with the tibial insert or is a discrete element from the tibial insert, can be in a fixed, non-variable position relative to the tibial base. Alternatively, in any of the prosthesis embodiments disclosed herein, particularly in total knee replacement prostheses, the a tibial insert can be in non-fixed, non-variable positions relative to a tibial baseplate. In other words, a prosthesis can be a mobile bearing implant in which the tibial insert is not in a fixed, non-variable position relative to the prosthesis's tibial base.

Figure 81A:
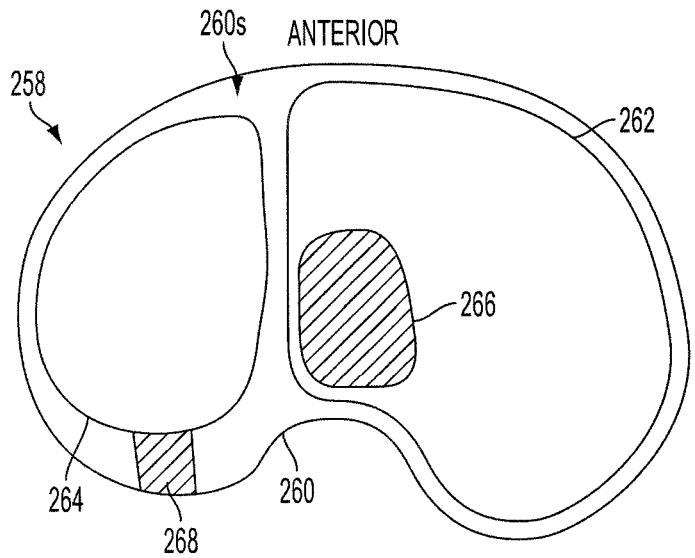
FIG. 81A is a top view of one embodiment of a tibial implant including a movable lateral tibial insert.
Figure 81B:
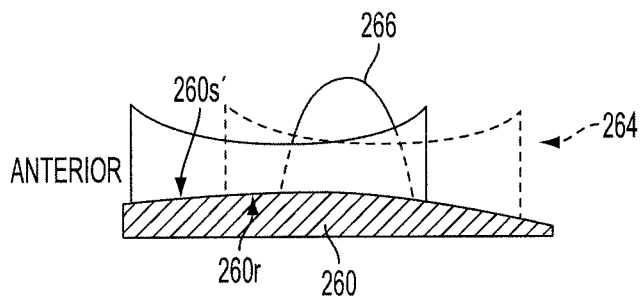
FIG. 81B is a side cross-sectional view of a portion of the tibial implant of FIG. 81A.
Figure 81C:
FIG. 81C is a side view of an embodiment of a tibial baseplate having a substantially flat top surface profile.
Figure 81D:
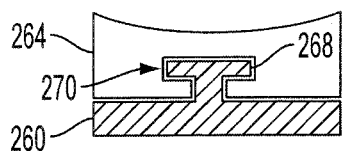
FIG. 81D is a coronal cross-sectional view of a portion of the tibial implant of FIG. 81A.
Figure 81E:
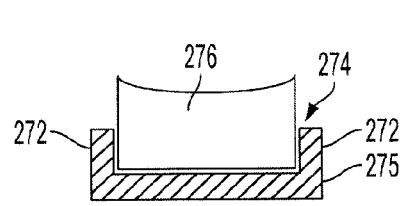
FIG. 81E is a coronal cross-sectional view of an embodiment of a tibial implant having a baseplate with a substantially flat profile.
Figure 81F:
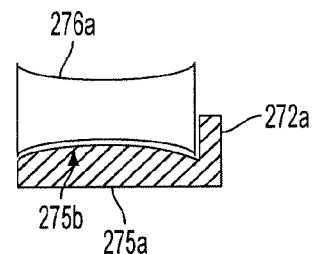
FIG. 81F is a coronal cross-sectional view of an embodiment of a tibial implant having a baseplate with a substantially convex profile.

As in an embodiment illustrated in FIGS. 81A, 81B, and 81D, a mobile bearing tibial insert 258 of a total knee replacement prosthesis can include a base, e.g., a baseplate 260, a medial tibial insert 262 fixedly coupled to the baseplate 260, and a lateral tibial insert 264 movably coupled to the baseplate 260 such that the lateral tibial insert 264 can move relative to the baseplate 260 and to the medial tibial insert 262. A tibial post 266 can be coupled, either integrally or as a discrete element, to the medial tibial insert 262. The lateral tibial insert 264 can therefore be movable relative to the post 266. The lateral tibial insert 264 can be movably coupled to the baseplate 260 in a variety of ways, such as by a rail/track system. The baseplate 260 includes an anterior-posterior rail 268, as shown in FIGS. 81A and 81D, and the lateral tibial insert 264 includes a rail 270, but the baseplate 260 could include a rail with the lateral tibial insert including a track. The rail/track in the illustrated embodiment has a T-shaped cross-section, but a rail/track system can have any cross-sectional shape. The lateral tibial insert 264 can be configured to be substantially conforming to a mating lateral femoral condyle, as shown in FIG. 81B. FIG. 81B also shows movable motion of the lateral tibial insert 264 relative to the baseplate 260 and the post 266 with the lateral tibial insert 264 in solid line in a first position and in dotted line in a second, different position. Only two different positions of the lateral tibial insert 264 is shown in FIG. 81B, but the lateral tibial insert 264 can be movable between any number of positions relative to the baseplate 260 and the post 266. A surface 260s of the baseplate 260, e.g., a top surface, to which the inserts 262, 264 can be coupled can have a convex profile in a sagittal view, as shown in FIG. 81B. The baseplate's convex profile can have a radius 260r, e.g., in a range of about 20 to 200 mm, in a range of about 60 to 200 mm, in a range of about 20 to 100 mm, etc. Alternatively, as shown in FIG. 81C, a surface 260s' of a baseplate 260' to which medial and lateral tibial inserts can be coupled can be substantially flat in a sagittal view. A tibial baseplate 275 including a substantially flat baseplate surface can, as shown in one embodiment in FIG. 81E, be movably coupled to a tibial insert by including opposed side rails 272 that define a channel 274 in which the tibial insert 276 can move. Similarly, a tibial baseplate 275a including a convex baseplate surface 275b can, as shown in one embodiment in FIG. 81F, be movably coupled to a tibial insert by including one side rail 272a that defines an interior guide surface along which a tibial insert 276a can move.

Figure 82A:
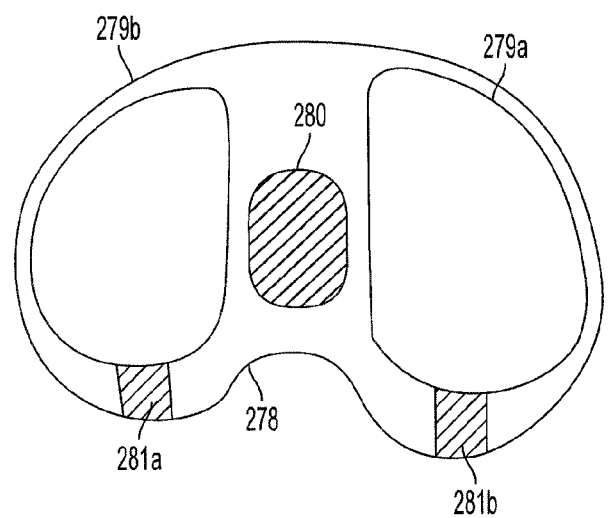
FIG. 82A is a top view of an embodiment of a tibial implant including a movable medial tibial insert and a movable lateral insert.

Although a tibial post can be coupled to a tibial insert coupled to a baseplate in a mobile bearing implant as discussed above, in another embodiment, a tibial post can be coupled to a baseplate, either integrally or as a separate element, while medial and/or lateral tibial inserts coupled to the baseplate can be movably coupled to the baseplate. In an exemplary embodiment, both the medial and lateral tibial inserts can be movably coupled to the baseplate. FIG. 82A illustrates one embodiment of a tibial baseplate 278 having a medial tibial insert 279a movably coupled thereto, a lateral tibial insert 279b movably coupled thereto, and a tibial post 280 non-movably coupled thereto either integrally or as a separate element. The medial and lateral tibial inserts 279a, 279b can therefore each be movable relative to the post 280 and relative to each other. The medial and lateral tibial inserts 279a, 279b can each be coupled to the baseplate 278 in any way, same or different from one another, such as by being movable within respective tracks 281a, 281b formed in the baseplate 278.

Figure 82B:
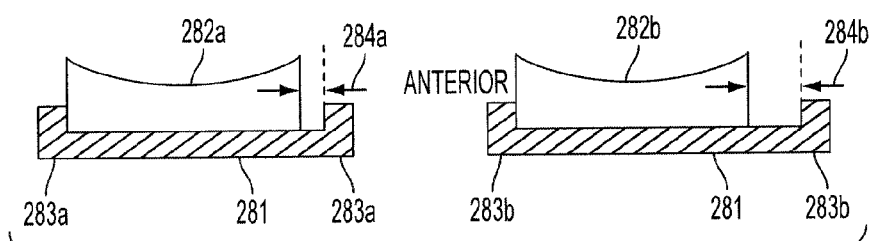
FIG. 82B is a side view of an embodiment of a tibial baseplate having a substantially flat top surface profile and opposed side rails for a medial tibial insert and opposed side rails for a lateral tibial insert.

In another embodiment, similar to that discussed above regarding a prosthesis including a tibial post coupled to a tibial insert coupled to a baseplate in a mobile bearing implant, a movable medial or lateral tibial insert can be movably coupled to a baseplate having a substantially flat top surface including opposed side rails defining a channel in which a tibial insert can move. The side rails for a lateral tibial insert can be a farther distance apart from one another than side rails for a medial tibial insert such that the medial tibial insert can be configured to undergo less anteroposterior translation compared to the lateral tibial insert. This movement can allow normal kinematics characterized by greater anteroposterior tibiofemoral motion in the lateral compartment of the knee. FIG. 82B illustrates an embodiment of a baseplate 281 including a substantially flat baseplate surface to which a medial tibial insert 282a and a lateral tibial insert 282b can be coupled. The surface can include anterior-poster opposed side rails 283a spaced a distance 284a apart from one another between which the medial tibial insert 282a can move and anterior-poster opposed side rails 283b spaced a farther distance 284b apart from one another between which the lateral tibial insert 282b. The side rails 283a, 283b can therefore be configured as anterior-posterior stops, e.g., one 283a located posteriorly and the other 283a located anteriorly and one 283b located posteriorly and the other 283b located anteriorly, so as to allow their associated tibial insert to move within a define anterior-posterior area.

Figure 82C:
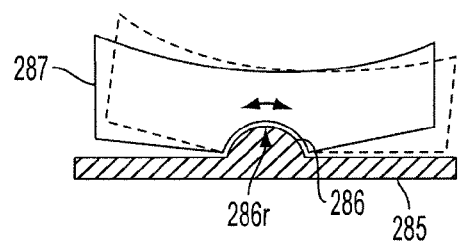
FIG. 82C is a side view of an embodiment of a tibial baseplate having a relatively small radius convex structure on a top surface thereof configured to movably mate a tibial insert thereto.
Figure 82D:
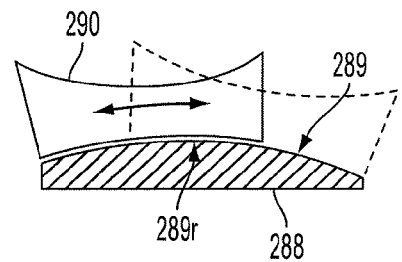
FIG. 82D is a side view of an embodiment of a tibial baseplate having a relatively large radius convex top surface thereof configured to movably mate a tibial insert thereto.

In another embodiment, a baseplate can include a protruding convex member on a top surface thereof configured to allow a tibial insert coupled to the baseplate to pivot thereabout. In one embodiment illustrated in FIG. 82C, a baseplate 285 can include a protruding convex member 286 about which a tibial insert 287, e.g., a medial tibial insert, can pivot. The protruding convex member 286 can have a relatively small radius 286r, e.g., in a range of about 3 to 30 mm. By having a relatively small radius 286r, the protruding convex member 286 can allow the tibial insert 287 to have relatively limited anteroposterior motion. FIG. 82C shows the tibial insert 287 in a solid line in a first position at one end of the insert's range of pivotal motion and in a dotted line in a second position at the other end of the insert's range of pivotal motion. FIG. 82D illustrates a baseplate 288 including a convex surface 289 to which a tibial insert 290, e.g., a lateral tibial insert, can mate and be movable relative thereto. The convex surface 289 can have a relatively large radius 289r, e.g., in a range of about 50 to 200 mm, which can allow for greater anterior-posterior motion to occur than with a smaller radius. FIG. 82D shows the tibial insert 290 in a solid line in a first position at one end of the insert's range of pivotal motion and in a dotted line in a second position at the other end of the insert's range of pivotal motion. A baseplate including the relatively small radius protruding convex member 286 of FIG. 82C for a medial tibial insert and the relatively large radius convex surface 289 of FIG. 82D for a lateral tibial insert can allow for greater mobility of medial relative to a lateral side of the tibia, which can allow for natural medial pivot kinetics.

EXAMPLES

The performance of an ACL-substituted CR prosthesis configured for total knee replacement surgery was compared with that of a conventional CR implant. Five different activities of a knee including the prosthesis were simulated, namely lunge, deep knee bend, chair rise/sit, stair ascent, and walking. These simulations were carried out using a Virtual Knee Simulator, available from LifeModeler® Inc. of San Clemente, Calif., and the motion of the medial and lateral flexion facet centers (FFC) were measured during each activity. In all simulations the ACL ligament was absent, while the PCL ligament was present. During all simulated activities, the ACL-substituted prosthesis showed kinematics close to that of healthy knees. In contrast, the conventional CR prosthesis showed abnormal posterior location of the femur at full extension and abnormal anterior sliding during early to mid-flexion for all the simulated activities.

Figure 64:
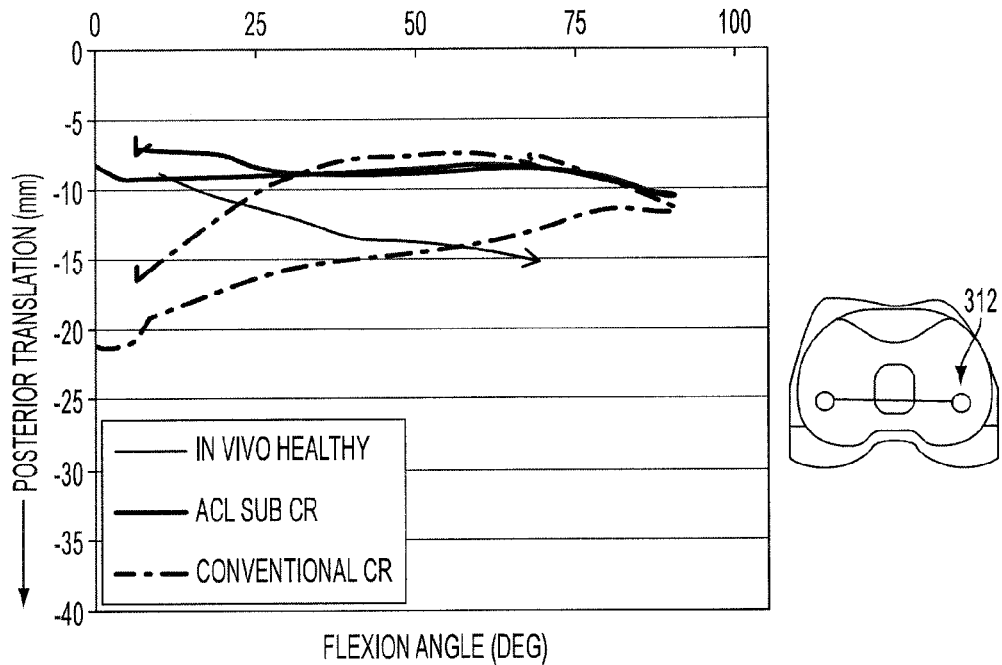
FIG. 64 is a graph showing motion of the medial FFC of the prosthesis of FIG. 58 as a function of knee flexion during a simulated stair ascent activity for the ACL-substituted CR implant and for a conventional CR implant.
Figure 65:
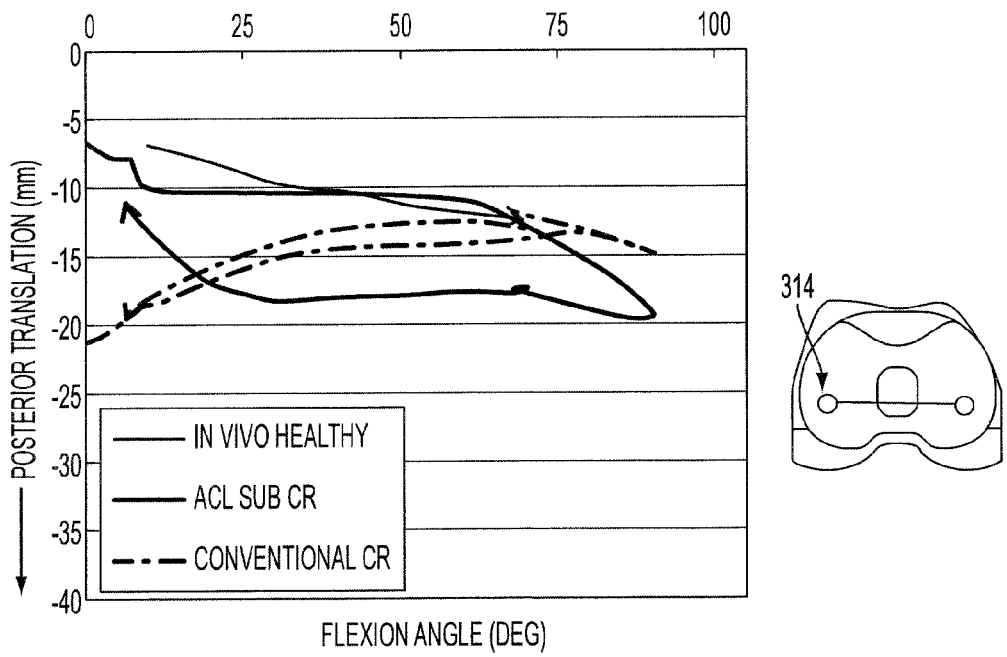
FIG. 65 is a graph showing motion of the lateral FFC of the prosthesis of FIG. 58 as a function of knee flexion during a simulated stair ascent activity for the ACL-substituted CR implant and for a conventional CR implant.
Figure 66:
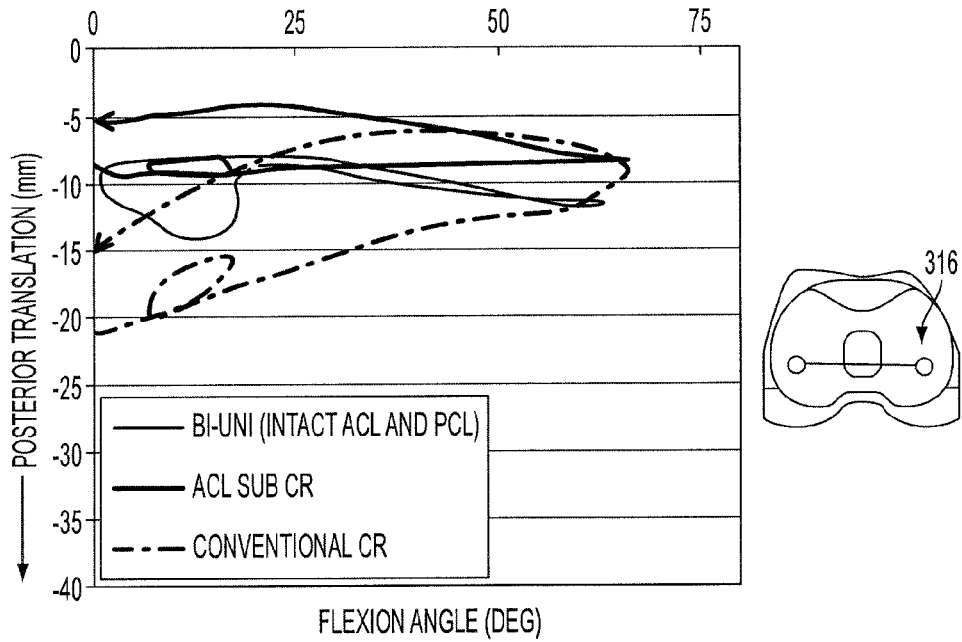
FIG. 66 is a graph showing motion of the medial FFC of the prosthesis of FIG. 58 as a function of knee flexion during simulated walking for the ACL-substituted CR implant and for a conventional CR implant.
Figure 67:
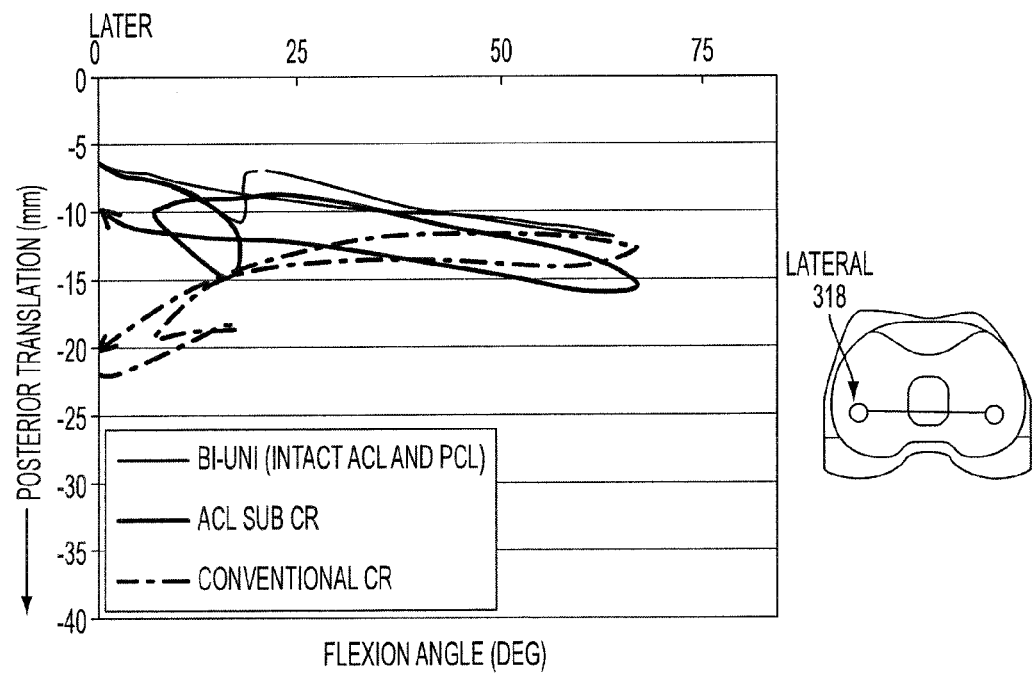
FIG. 67 is a graph showing motion of the lateral FFC of the prosthesis of FIG. 58 as a function of knee flexion during simulated walking for the ACL-substituted CR implant and for a conventional CR implant.

FIGS. 58-67 illustrate the prosthesis along with various graphical results of the comparisons. Generally, FIGS. 58-65 illustrate results of simulations for the lunge, deep knee bend, and chair rise/sit activities with reference to in vivo knee motion data for healthy subjects variously extracted from Johal et al., "Tibio-Femoral Movement In The Living Knee: A Study Of Weight Bearing And Non-Weight Bearing Knee," J Biomech. 2005 February, 38(2):269-76; Komistek et al., "In Vivo Fluoroscopic Analysis Of The Normal Human Knee," Clin Orthop Relat Res. 2003 May, (410):69-81; and Morooka, et al., "Dynamic Activity Dependence Of In Vivo Normal Knee Kinematics," J Orthop Res. 2008 April, 26(4):428-34. Generally, FIGS. 66 and 67 illustrate graphs showing results of simulated walking with reference to in vivo knee motion data for patients who received bi-unicondylar implants that preserve both the ACL and PCL ligaments extracted from Banks et al., "Comparing In Vivo Kinematics Of Unicondylar And Bi-Unicondylar Knee Replacements," Knee Surg Sports Traumatol Arthrosc. 2005 Oct. 13(7):551-6.

Figure 58:
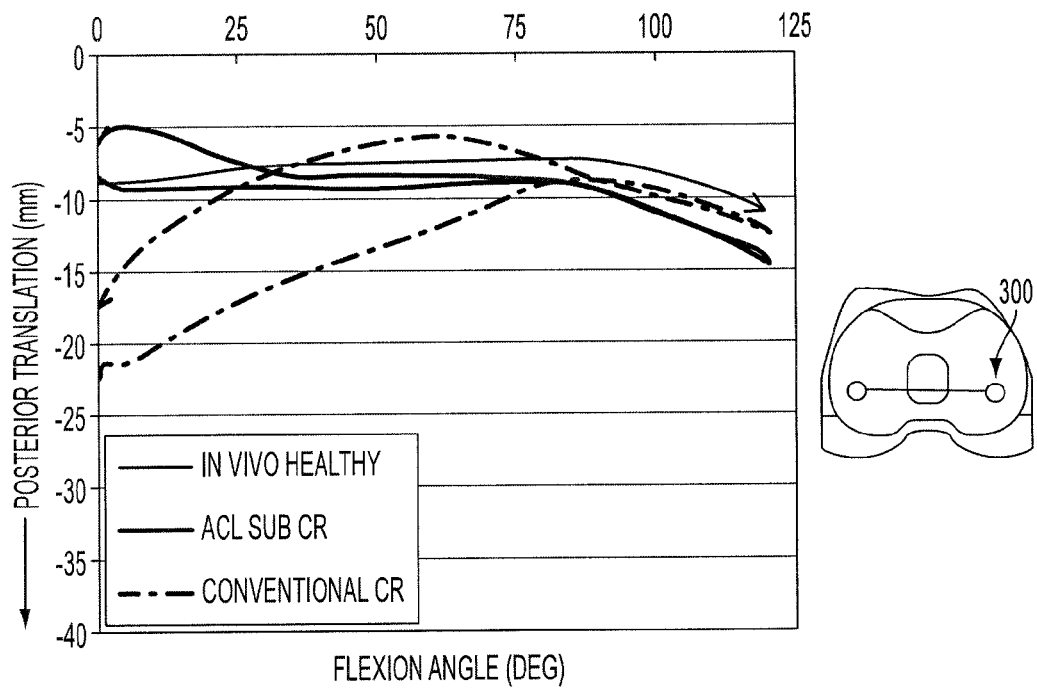
FIG. 58 is a graph showing motion of a medial flexion facet center (FFC) of a total knee replacement prosthesis as a function of knee flexion during a simulated lunge activity for a ACL-substituted CR implant of the prosthesis and for a conventional CR implant.
Figure 59:
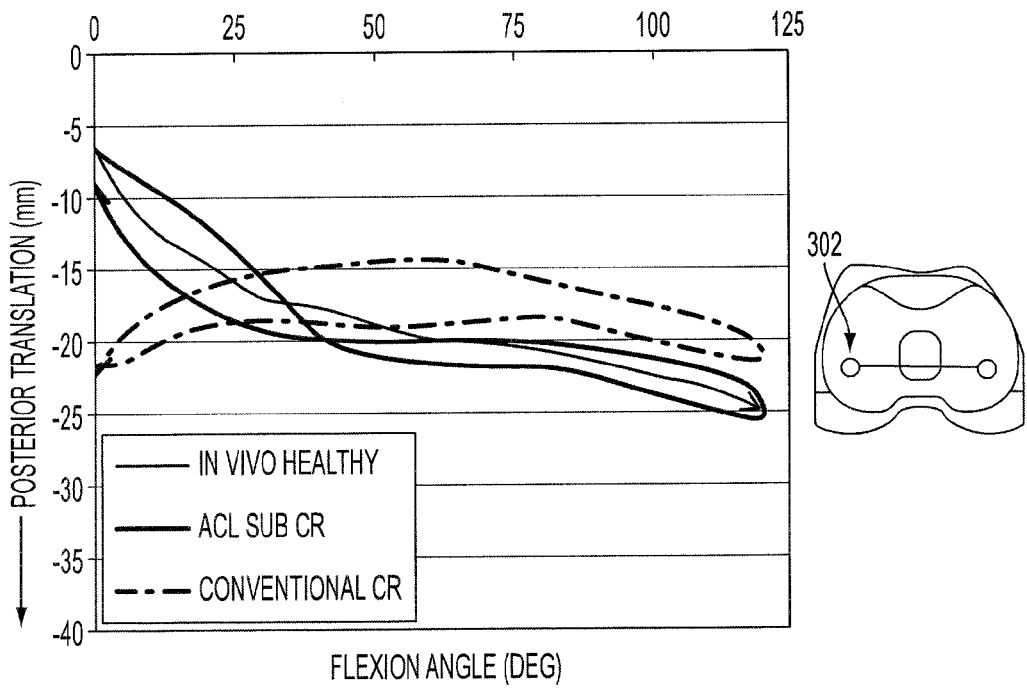
FIG. 59 is a graph showing motion of a lateral FFC of the prosthesis of FIG. 58 as a function of knee flexion during a simulated lunge activity for the ACL-substituted CR implant and for a conventional CR implant.

FIGS. 58 and 59 illustrate graphical results of motion during simulated lunge activity, one cycle of flexion from 0° to 120° and one cycle of extension from 120° to 0°, with reference to healthy subject data from Johal et al., referenced above. FIG. 58 shows the motion of the medial FFC 300 as a function of knee flexion angle during a lunge activity. The medial FFC in the conventional CR implant was shifted posteriorly at full extension and showed abnormal anterior sliding in early to mid-flexion, e.g., from 0° to 50°. In contrast, the ACL-substituted CR prosthesis showed more normal medial FFC motion, with minimal anterior-posterior translation until 90° flexion followed by posterior translation at higher flexion angles. FIG. 59 shows the motion of the lateral FFC 302 as a function of knee flexion angle during a simulated lunge activity. The lateral FFC in the conventional CR implant was again shifted posteriorly at full extension and showed abnormal anterior sliding during early to mid-flexion. In contrast, the ACL-substituted CR prosthesis showed kinematics very close to the in vivo kinematics of healthy knees.

Figure 60:
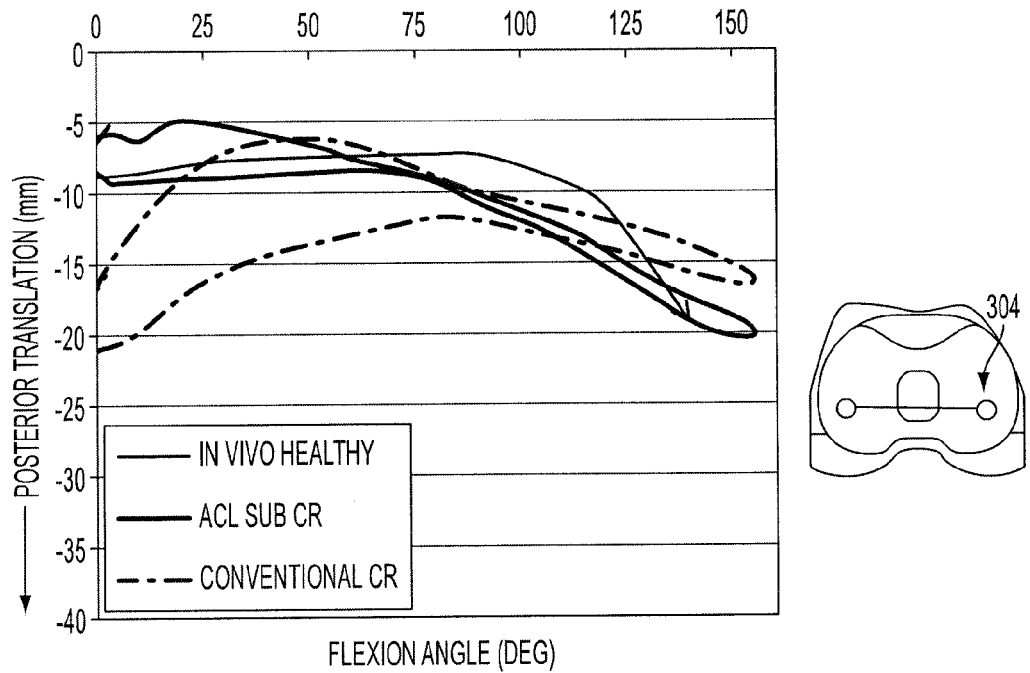
FIG. 60 is a graph showing motion of the medial FFC of the prosthesis of FIG. 58 as a function of knee flexion during a simulated deep knee bending activity for the ACL-substituted CR implant and for a conventional CR implant.
Figure 61:
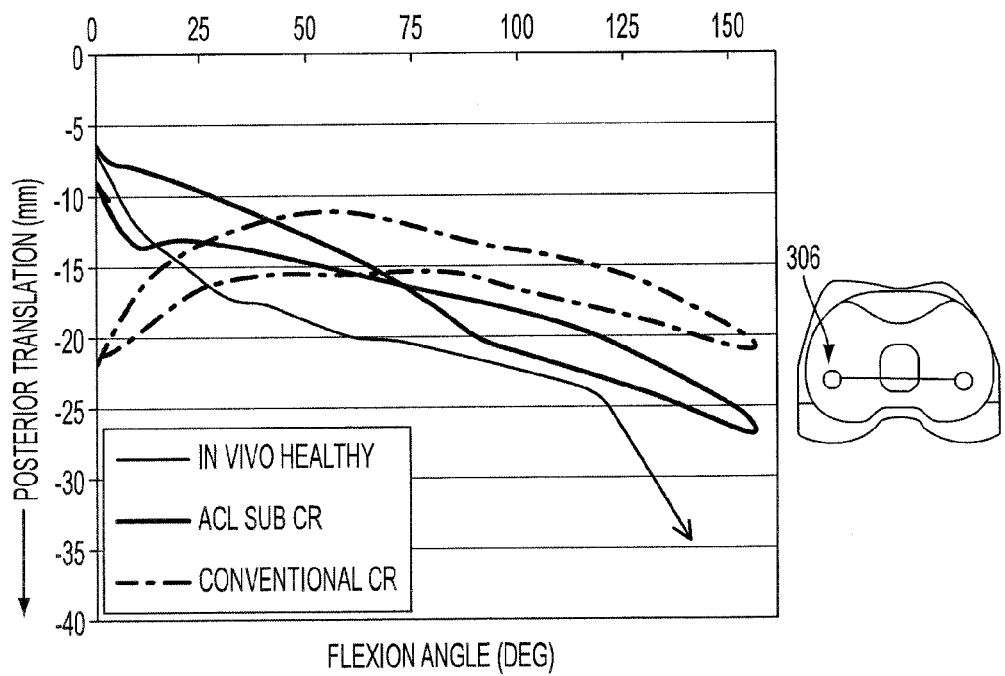
FIG. 61 is a graph showing motion of the lateral FFC of the prosthesis of FIG. 58 as a function of knee flexion during a simulated deep knee bending activity for the ACL-substituted CR implant and for a conventional CR implant.

FIGS. 60 and 61 illustrate graphical results of motion during simulated deep knee bend activity, one cycle of flexion from 0° to 155° and one cycle of extension from 155° to 0°, with reference to healthy subject data from Johal et al., referenced above. FIG. 60 shows the motion of the medial FFC 304 as a function of knee flexion angle during a deep knee bending activity. The medial FFC in the conventional CR implant was shifted posteriorly at full extension and showed paradoxical anterior sliding in a mid-flexion range, e.g., from about 0° to 55°. In contrast, the ACL-substituted CR prosthesis showed more normal medial FFC motion, with minimal anterior-posterior motion until 85° flexion followed by posterior translation at higher flexion angles. FIG. 61 shows the motion of the lateral FFC 306 as a function of knee flexion angle during a simulated deep knee bending activity. The lateral FFC in the conventional CR implant was again dislocated posteriorly at full extension and showed paradoxical anterior sliding in the mid-flexion range. On the other hand, the ACL-substituted CR prosthesis showed kinematics closely mimicking the in vivo kinematics of healthy knees.

Figure 62:
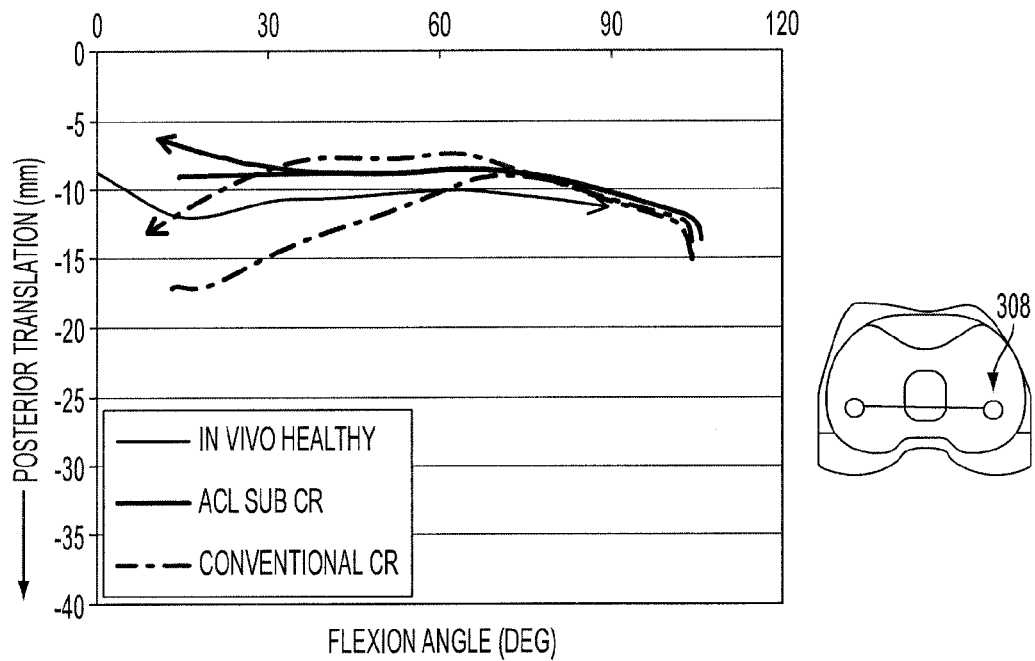
FIG. 62 is a graph showing motion of the medial FFC of the prosthesis of FIG. 58 as a function of knee flexion during a simulated chair rise/sit activity for the ACL-substituted CR implant and for a conventional CR implant.
Figure 63:
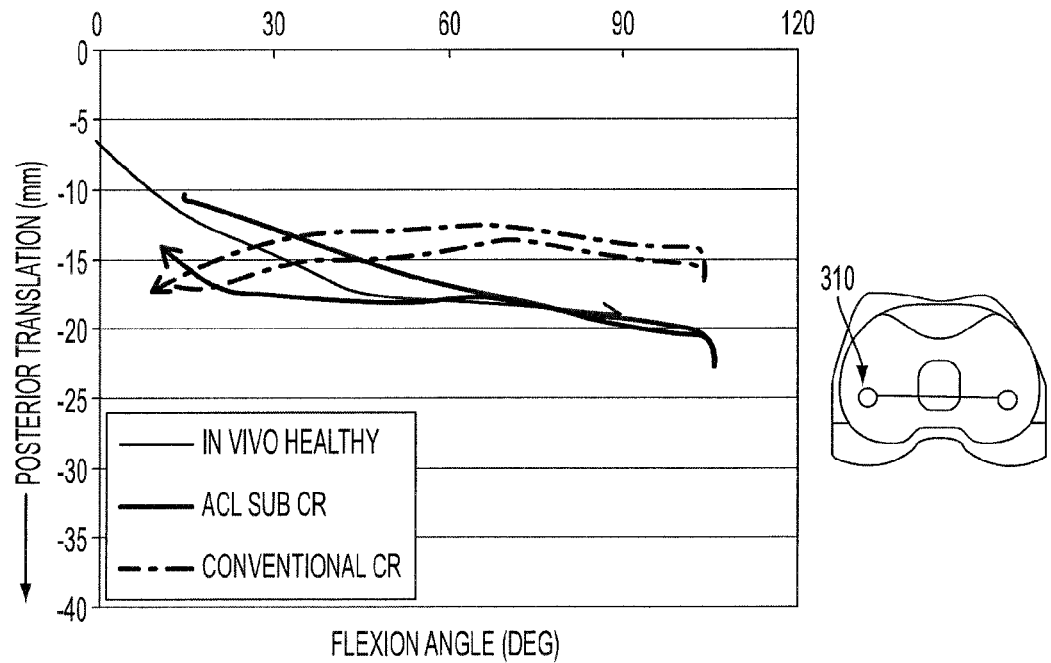
FIG. 63 is a graph showing motion of the lateral FFC of the prosthesis of FIG. 58 as a function of knee flexion during a simulated chair rise/sit activity for the ACL-substituted CR implant and for a conventional CR implant.

FIGS. 62 and 63 illustrate graphical results of motion during simulated rising from and sitting into a chair, one full cycle from 10° to 105° flexion and from 10° to 105° flexion, with reference to healthy subject data from Komistek et al., referenced above. Similar to the lunge and deep knee bending activities, the medial FFC of the conventional CR prosthesis again showed abnormal posterior location and anterior sliding during a simulated chair rise/sit activity, as shown in FIG. 62. The motion of the medial FFC 308 for the ACL-substituted CR prosthesis was much more consistent with the in vivo data. Like the medial FFC, the lateral FFC for the conventional CR prosthesis showed abnormal posterior location at full extension followed by anterior sliding, as shown in FIG. 63. In contrast, the lateral FFC 310 of the ACL-substituted prosthesis showed posterior rollback of the lateral FFC consistent with in vivo data.

FIGS. 64 and 65 illustrate graphical results of motion during simulated stair ascent, one full cycle from 0° to 90° flexion and from 90° to 0° flexion, with reference to healthy subject data from Moro-oka et al., referenced above. FIG. 64 shows that during the simulated stair ascent, the medial FFC of the conventional CR prosthesis showed abnormal posterior location at full extension, followed by anterior sliding. The motion of the medial FFC 312 motion for the ACL-substituted CR prosthesis was much more stable, although it did not show the posterior rollback seen in the in vivo data. Like the medial FFC, the lateral FFC for the conventional CR prosthesis also showed abnormal posterior location at full extension followed by anterior sliding, as shown in FIG. 65. In contrast, the lateral FFC 314 of the ACL-substituted prosthesis showed posterior rollback consistent with in vivo data.

FIGS. 66 and 67 illustrate graphical results of motion during simulated walking, one full gait cycle going from 0° to 65° flexion and from 65° to 0° flexion, with reference to data from Banks et al., referenced above. FIG. 66 shows the motion of the medial FFC as a function of knee flexion angle during simulated walking. The medial FFC in the conventional CR implant was located posteriorly at full extension and showed significant anterior sliding during flexion. In contrast, the ACL-substituted CR prosthesis showed more stable medial FFC 316 motion, similar to that seen in vivo for patients with ACL and PCL preserving implants. FIG. 67 shows the motion of the lateral flexion facet center as a function of knee flexion angle during simulated walking. The lateral FFC in the conventional CR implant was again located posteriorly at full extension and showed abnormal anterior sliding with flexion. In contrast, the ACL-substituted CR prosthesis showed lateral FFC 318 motion similar to that seen in vivo for patients with ACL and PCL preserving implants.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical device, comprising:
   a tibial implant having an inferior surface and an opposite, superior surface, the inferior surface being configured to be fixed to a tibia of a patient;
   a femoral implant mateable to the tibial implant and having an inferior surface and an opposite, superior surface, the superior surface being configured to be fixed to a femur of the patient, and the tibial implant being configured to articulate relative to the femoral implant when the tibial implant is fixed to the tibia and the femoral implant is fixed to the femur; and
   a post extending from the superior surface of the tibial implant near an edge thereof, the post being configured to be substantially centered on the tibia when the tibial implant is fixed thereto such that the post simulates an anterior cruciate ligament (ACL) when the tibial implant is fixed to the tibia and the femoral implant is fixed to the femur,
   wherein the tibial implant has a lateral compartment configured to be seated on a lateral surface of the tibia with a first portion of the tibial implant being seated on or over the tibia's lateral surface and a second, substantially smaller portion of the tibial implant being seated on or over the tibia's medial surface.

2. The device of claim 1, wherein the post is asymmetric about one or more of sagittal, coronal, and transverse planes.

3. The device of claim 1, wherein the post is integrally formed with the tibial implant.

4. The device of claim 1, wherein the post is a discrete element configured to couple to the tibial implant.

5. The device of claim 1, further comprising a femoral notch structure coupled to the femoral implant, the femoral notch structure being configured to prevent the post from impinging on a lateral surface of the femur through a full range of knee flexion when the tibial implant is fixed to the tibia and the femoral implant is fixed to the femur.

6. The device of claim 5, wherein the post is configured to articulate relative to the femoral notch structure.

* * * * *